(12) United States Patent
Struck et al.

(10) Patent No.: US 9,777,160 B2
(45) Date of Patent: Oct. 3, 2017

(54) COPPER-CONTAINING METAL PIGMENTS WITH A METAL OXIDE LAYER AND A PLASTIC LAYER, METHOD FOR THE PRODUCTION THEREOF, COATING AGENT AND COATED OBJECT

(75) Inventors: Oliver Struck, Henfenfeld (DE); Phu Qui Nguyen, Moenchengladbach (DE); Dirk Schumacher, Pegnitz (DE); Sebastian Hoefener, Nuremberg (DE)

(73) Assignee: ECKART GMBH, Hartenstein (DE)

( * ) Notice: Subject to any disclaimer, the term of this patent is extended or adjusted under 35 U.S.C. 154(b) by 0 days.

(21) Appl. No.: 14/007,300

(22) PCT Filed: Mar. 21, 2012

(86) PCT No.: PCT/EP2012/054961
§ 371 (c)(1),
(2), (4) Date: Oct. 29, 2013

(87) PCT Pub. No.: WO2012/130680
PCT Pub. Date: Oct. 4, 2012

(65) Prior Publication Data
US 2014/0050768 A1 Feb. 20, 2014

(30) Foreign Application Priority Data

Mar. 25, 2011 (DE) .................. 10 2011 001 575
May 27, 2011 (DE) .................. 10 2011 103 882

(51) Int. Cl.
| | |
|---|---|
| C09C 1/62 | (2006.01) |
| A61Q 19/00 | (2006.01) |
| C09D 7/12 | (2006.01) |
| A61K 8/02 | (2006.01) |
| C09C 1/00 | (2006.01) |
| C09C 1/66 | (2006.01) |
| A61Q 1/04 | (2006.01) |
| A61Q 1/06 | (2006.01) |
| A61Q 1/10 | (2006.01) |
| A61Q 1/12 | (2006.01) |
| A61Q 3/02 | (2006.01) |
| A61Q 5/06 | (2006.01) |
| A61K 8/81 | (2006.01) |
| A61Q 19/10 | (2006.01) |
| A61K 8/19 | (2006.01) |
| C08K 9/02 | (2006.01) |
| C08K 9/10 | (2006.01) |
| C08K 3/08 | (2006.01) |

(52) U.S. Cl.
CPC ............ *C09C 1/627* (2013.01); *A61K 8/0258* (2013.01); *A61K 8/0262* (2013.01); *A61K 8/19* (2013.01); *A61K 8/8152* (2013.01); *A61Q 1/04* (2013.01); *A61Q 1/06* (2013.01); *A61Q 1/10* (2013.01); *A61Q 1/12* (2013.01); *A61Q 3/02* (2013.01); *A61Q 5/06* (2013.01); *A61Q 19/00* (2013.01); *A61Q 19/10* (2013.01); *C09C 1/0021* (2013.01); *C09C 1/66* (2013.01); *C09D 7/1225* (2013.01); *C09D 7/1291* (2013.01); *A61K 2800/43* (2013.01); *A61K 2800/621* (2013.01); *A61K 2800/624* (2013.01); *A61K 2800/63* (2013.01); *A61K 2800/651* (2013.01); *C08K 9/02* (2013.01); *C08K 9/10* (2013.01); *C08K 2003/085* (2013.01); *C09C 2200/1054* (2013.01); *C09C 2200/1058* (2013.01); *C09C 2200/405* (2013.01)

(58) Field of Classification Search
CPC ........ A61K 8/0258; C09C 1/627; C09C 1/66; C09C 2200/1054
See application file for complete search history.

(56) References Cited

U.S. PATENT DOCUMENTS

| | | |
|---|---|---|
| 2,071,250 A | 2/1937 | Carothers |
| 2,071,251 A | 2/1937 | Carothers |
| 2,130,523 A | 9/1938 | Carothers |
| 2,130,948 A | 9/1938 | Carothers |
| 2,241,322 A | 5/1941 | Hanford |
| 2,312,966 A | 3/1948 | Hanford |
| 2,512,606 A | 6/1950 | Bolton et al. |
| 3,055,859 A | 9/1962 | Bruno Vollmert |
| 3,393,210 A | 7/1968 | Speck |
| 3,530,094 A | 9/1970 | Schnell et al. |

(Continued)

FOREIGN PATENT DOCUMENTS

| | | |
|---|---|---|
| DE | 1 495 730 A | 4/1969 |
| DE | 1 300 266 B | 7/1969 |

(Continued)

*Primary Examiner* — Anna Falkowitz
(74) *Attorney, Agent, or Firm* — The Webb Law Firm

(57) ABSTRACT

The invention relates to copper-containing metal pigments, wherein the copper-containing metal pigments have an elemental copper content of at least 50 wt.-%, relative to the total weight of the uncoated copper-containing metal pigment, wherein the copper-containing metal pigments have at least one enveloping metal oxide layer and at least one enveloping chemically non-reactive plastic layer, wherein the sum of the amounts of the at least one chemically non-reactive plastic layer and of the at least one metal oxide layer lies in a range of from 10 to 50 wt.-%, relative to the weight of the uncoated metal pigment, and the weight ratio of the at least one metal oxide layer to the at least one chemically non-reactive plastic layer lies in a range of from 1:2 to 1:20. The invention furthermore relates to a method for producing these pigments and the use thereof.

27 Claims, No Drawings

(56) References Cited

U.S. PATENT DOCUMENTS

| | | | |
|---|---|---|---|
| 3,535,280 | A | 10/1970 | Schnell et al. |
| 4,224,419 | A | 9/1980 | Swoboda et al. |
| 4,537,949 | A | 8/1985 | Schmidt et al. |
| 4,540,772 | A | 9/1985 | Pipper et al. |
| 4,750,940 | A | 6/1988 | Higashi et al. |
| 4,788,253 | A | 11/1988 | Hambrecht et al. |
| 4,957,965 | A | 9/1990 | Taubitz et al. |
| 4,970,255 | A | 11/1990 | Reimann et al. |
| 5,332,767 | A | 7/1994 | Reisser et al. |
| 6,323,279 | B1 | 11/2001 | Guntherberg et al. |
| 7,172,812 | B2 | 2/2007 | Greiwe et al. |
| 7,485,365 | B2 | 2/2009 | Schuster et al. |
| 8,157,909 | B2 | 4/2012 | Wczasek et al. |
| 2006/0032403 | A1 | 2/2006 | Kaupp et al. |
| 2007/0243149 | A1 | 10/2007 | Hofacker et al. |
| 2008/0249209 | A1 | 10/2008 | Trummer et al. |
| 2008/0295737 | A1 | 12/2008 | Henglein et al. |
| 2009/0117281 | A1 | 5/2009 | Sato et al. |
| 2009/0264575 | A1* | 10/2009 | Henglein et al. ............. 524/441 |
| 2010/0152355 | A1 | 6/2010 | Schumacher et al. |
| 2010/0163420 | A1* | 7/2010 | Weiss et al. .................... 205/80 |
| 2011/0293547 | A1 | 12/2011 | Geissler et al. |
| 2013/0058988 | A1 | 3/2013 | Winkelmann et al. |

FOREIGN PATENT DOCUMENTS

| | | | | |
|---|---|---|---|---|
| DE | 31 47 177 A1 | | 6/1983 | |
| DE | 36 30 356 A1 | | 3/1987 | |
| DE | 40 30 727 A1 | | 4/1992 | |
| DE | 197 28 629 A1 | | 1/1999 | |
| DE | 198 20 112 A1 | | 11/1999 | |
| DE | 102 38 090 A1 | | 3/2004 | |
| DE | 103 61 437 A1 | | 7/2005 | |
| DE | 10 2005 037 611 A1 | | 2/2007 | |
| DE | 10 2005 061 684 A1 | | 6/2007 | |
| DE | WO 2008/052720 | * | 5/2008 | |
| DE | 10 2007 006 820 A1 | | 8/2008 | |
| DE | 10 2009 006 550 A1 | | 7/2010 | |
| DE | 10 2010 020 507 A1 | | 11/2011 | |
| EP | 0 038 094 B1 | | 10/1981 | |
| EP | 0 038 582 B1 | | 10/1981 | |
| EP | 0 039 524 B2 | | 11/1981 | |
| EP | 0 099 532 A2 | | 2/1984 | |
| EP | 0 113 112 B1 | | 7/1984 | |
| EP | 0 129 195 B1 | | 12/1984 | |
| EP | 0 129 196 B1 | | 12/1984 | |
| EP | 0 135 130 A2 | | 3/1985 | |
| EP | 0 299 444 B2 | | 1/1989 | |
| EP | 0 302 485 A3 | | 2/1989 | |
| EP | 1 529 084 B1 | | 5/2005 | |
| EP | 1 529 085 B1 | | 5/2005 | |
| EP | 1 812 519 B1 | | 8/2007 | |
| EP | WO 2009/135784 | * | 11/2009 | ............... C09C 1/00 |
| EP | WO2009/135784 | * | 11/2009 | ............. C09C 1/100 |
| WO | 2005/063897 A2 | | 7/2005 | |
| WO | 2007/017195 A3 | | 2/2007 | |
| WO | 2007/115675 A2 | | 10/2007 | |
| WO | 2008/095697 A1 | | 8/2008 | |
| WO | 2009/135784 A1 | | 11/2009 | |
| WO | 2009/149834 A3 | | 12/2009 | |
| WO | 2009/152941 A3 | | 12/2009 | |

* cited by examiner

US 9,777,160 B2

COPPER-CONTAINING METAL PIGMENTS WITH A METAL OXIDE LAYER AND A PLASTIC LAYER, METHOD FOR THE PRODUCTION THEREOF, COATING AGENT AND COATED OBJECT

CROSS-REFERENCE TO RELATED APPLICATIONS

This application is the national phase of PCT/EP2012/054961 filed Mar. 21, 2012 and claims priority to German Patent Application No. 10 2011 001 575.2, filed Mar. 25, 2011 and German Patent Application No. 10 2011 103 882.9, filed May 27, 2011, the entire disclosures of which are herein incorporated by reference.

BACKGROUND OF THE INVENTION

Field of the Invention

The invention relates to copper-containing metal pigments with at least one enveloping metal oxide layer and at least one enveloping plastic layer, as well as a method for the production thereof. The invention furthermore relates to a coating agent, as well as a coated object.

Description of Related Art

Copper-containing metal pigments, in particular metallic effect pigments, such as copper pigments or brass pigments, which are also called gold bronze pigments, are often used in the graphics industry, for example in printer inks.

Copper-containing metal pigments are problematic to use because of their copper content. Copper-containing pigments, for example copper-containing metallic effect pigments, readily release Cu(I) ions to the surroundings, for example a varnish or a paint. The Cu(I) ions readily change into Cu(II) under the influence of moisture. The change in the oxidation state from Cu(I) to Cu(II) is necessarily accompanied by a reduction of components of the surroundings, for example of binder components of a varnish or a paint.

In addition, in particular Cu(II) ions form colored complexes which can have a disruptive effect on the hue of the corresponding application. For example, Cu(II) ions form intensely blue copper complexes under alkaline conditions, in particular in the presence of amines.

Above all, however, the Cu(II) ions, and in the case of gold bronze pigments also of Zn(II) ions, can bring about a gelling of the binder, which makes the corresponding application unusable.

For this reason, for example copper or gold bronze pigments which are coated with $SiO_2$ according to IDE 102 38 090 A1 cannot be reliably used in nail polishes.

The above-named effects are associated specifically with copper-containing metal pigments, and therefore have no counterpart in other metal pigments, for example in metal pigments consisting of aluminum, iron, tin, etc.

According to the teaching of WO 2009/149834 A2, copper-containing metallic effect pigments as well as coating agents with copper-containing metallic effect pigments are provided in which the above-named copper-specific problems are solved in that a cellulose derivative, selected from the group consisting of alkyl cellulose, hydroxyalkyl cellulose, alkyl(hydroxyalkyl) cellulose and mixtures thereof, is present as a further component.

These special cellulose derivatives can theoretically be added to liquid coating agents such as printer inks, varnishes or paints. However, for example incompatibilities often prevent the use of such cellulose derivatives.

WO 2007/017195 A2 discloses in general metallic effect pigments with a coating. The coating is characterized in that it comprises a mixed inorganic/organic layer. The mixed layer contains an inorganic network and at least one organic component, wherein the organic component is an organic oligomer and/or polymer which is at least partially covalently bonded to the inorganic network via one or more organic network formers.

It has been shown that the production of mixed inorganic/organic layers is expensive in terms of process technology.

Metallic effect pigments with a coating are also known in general from WO 2005/063897 A2. These metallic effect pigments are coated with oligomeric and/or polymeric binders that can be chemically cross-linked and/or can be cross-linked under the action of heat, IR radiation, UV radiation and/or electron beams. This still chemically reactive binder coating allows a reaction with the binder of a varnish or a printer ink after application of the metal pigment. A pre-coating with $SiO_2$ can be arranged under the binder coating.

It has been shown that, in the case of copper-containing metal pigments with the coating known from WO 2005/063897 with a not yet cross-linked binder coating, the release of copper ions to the surroundings is not reliably prevented. In addition, relatively large quantities of binder have to be used for the coating, which leads e.g. to a reduced covering capacity.

DE 198 20 112 A1 discloses effect pigments coated with reactive orientation additives. The subject of this application essentially consists of aluminum effect pigments which can be coated with a coating of metal oxides or polymers. Orientation additives which enable a covalent bonding to the binder of a paint or a varnish are then arranged on this coating.

Finally, metallic effect pigments coated with synthetic resin, in particular aluminum effect pigments, are known from DE 40 30 727 A1.

A double coating of $SiO_2$ and a synthetic resin of metallic effect pigments is known from US 2009/0117281 A1. This coating makes it possible to use the metal pigments in aqueous formulations and brings about an improved chemicals stability and water resistance of the films to which it has been applied. US 2009/0117281 A1 is clearly aimed at the use of aluminum effect pigments.

Metallic effect pigments with improved chemicals stability are also described in WO 2008/095697 A1.

With the exception of WO 2009/149834 A2 and WO 2008/095697 A1, the above-listed state of the art relates fundamentally to the coating of aluminum effect pigments, in order to provide corrosion-stable aluminum effect pigments.

Apart from WO 2009/149834 A2, none of the above-named documents from the state of the art addresses the problem that copper-containing pigments release copper ions, which can then lead to undesired effects, to the surroundings.

SUMMARY OF THE INVENTION

In some non-limiting embodiments, there is provided a platelet-shaped copper-containing metal pigment which has an elemental copper content of at least 50 weight percent, relative to the weight of an uncoated copper-containing metal pigment, wherein the copper-containing metal pigment comprises a coating comprising at least one enveloping metal oxide layer and at least one enveloping chemically non-reactive plastic layer, wherein the sum of the amounts of the at least one chemically non-reactive plastic layer and of the at least one metal oxide layer lies in a range of from 10 to 50 weight percent, relative to the weight of the uncoated metal pigment, and the weight ratio of the at least one metal oxide layer to the at least one chemically non-reactive plastic layer lies in a range of from 1:2 to 1:20.

In some non-limiting embodiments, there is provided a method for producing a platelet-shaped copper-containing metal pigment according to claim 1, comprising:

(1a) coating platelet-shaped copper-containing metal pigment with metal oxide, (1b) coating the platelet-shaped copper-containing metal pigment coated with metal oxide obtained in step (1a) with the educt(s) of a chemically non-reactive plastic layer, (1c) curing or polymerizing the copper-containing metal pigment coated with the educt(s) of the chemically non-reactive plastic layer in step (1 b), or (2a) coating platelet-shaped copper-containing metal pigment with the educt(s) of a chemically non-reactive plastic layer, (2b) curing or polymerizing the platelet-shaped copper-containing metal pigment coated with the educt(s) of the chemically non-reactive plastic layer in step (2a), (2c) coating the platelet-shaped copper-containing metal pigment coated with chemically non-reactive plastic layer obtained in step (2b) with metal oxide.

Also provided are pigmented coating agents, coated objects, cosmetic products, and methods for making the same, comprising the platelet-shaped copper-containing metal pigment of the present invention.

DETAILED DESCRIPTION

The object of the present invention is therefore to provide copper-containing metal pigments, in particular metallic effect pigments, which are stabilized such that no disadvantageous quantities of copper ions are released to the surroundings. For example, such disadvantageous quantities of copper ions discolor nail polish green, allow it to gel or make redispersal by means of shaking impossible.

Furthermore the copper-containing metal pigments according to the invention are to sustain as little damage as possible, preferably none, to other application-specific properties such as for example covering capacity, color, etc. e.g. during the process of baking a powder coating or a coil coating.

Furthermore, a further object is to provide coating agents which contain the copper-containing metal pigments according to the invention and sustain as little as possible, preferably none, of the above-named damage to application-specific properties.

In addition, the object of the present invention is to provide a coated object which contains or has the platelet-shaped copper-containing metal pigments according to the invention or which contains or has the above-named coating agent according to the invention and sustains as little as possible, preferably none, of the above-named damage to application-specific properties.

A further object of the invention is to provide copper-containing metal pigments, in particular metallic effect pigments, which can be produced in a simple manner in terms of process technology.

The object on which the invention is based is achieved by providing platelet-shaped copper-containing metal pigments, wherein the platelet-shaped copper-containing metal pigments have an elemental copper content of at least 50 wt.-%, relative to the weight of the uncoated copper-containing metal pigment, and wherein the copper-containing metal pigments have at least one enveloping metal oxide layer and at least one enveloping chemically non-reactive plastic layer, and the sum of the amount of the at least one chemically non-reactive plastic layer and the amount of the at least one chemically non-reactive metal oxide layer lies in a range of from 10 to 50 wt.-%, relative to the weight of the uncoated metal pigment, and the weight ratio of the at least one metal oxide layer to the at least one chemically non-reactive plastic layer lies in a range of from 1:2 to 1:20.

Preferred developments of the platelet-shaped copper-containing metal pigments according to the invention are given in dependent claims 2 to 18.

Furthermore, the object on which the invention is based is achieved by a coating agent which contains the platelet-shaped copper-containing metal pigments according to the invention.

In addition, the object on which the invention is based is achieved by a coated object which contains or has the platelet-shaped copper-containing metal pigments according to the invention or which contains or has the above-named coating agent according to the invention.

The object on which the invention is based is also achieved by the use of the platelet-shaped copper-containing metal pigments according to the invention in a coating agent.

The object on which the invention is based is furthermore achieved by providing a method for producing one of the platelet-shaped copper-containing metal pigments according to the invention which comprises the following steps:

(1a) coating platelet-shaped copper-containing metal pigments with metal oxide, (1b) coating the platelet-shaped copper-containing metal pigments coated with metal oxide obtained in step (1a) with the educt(s) of the chemically non-reactive plastic layer, (1c) curing or polymerizing the copper-containing metal pigments coated with the educt(s) of the chemically non-reactive plastic layer in step (1b), or (2a) coating the platelet-shaped copper-containing metal pigments with the educt(s) of the chemically non-reactive plastic layer, (2b) curing or polymerizing the platelet-shaped copper-containing metal pigments coated with the educt(s) of the chemically non-reactive plastic layer in step (2a), (2c) coating the platelet-shaped copper-containing metal pigments coated chemically non-reactive plastic layer obtained in step (2b) with metal oxide.

The sum of the amount of the at least one chemically non-reactive plastic layer and the amount of the at least one chemically non-reactive metal oxide layer necessarily lies in a range of from 10 to 50 wt.-%, relative to the weight of the uncoated metal pigment. Within this range, the weight ratio of the at least one metal oxide layer to the at least one chemically non-reactive plastic layer lies in a range of from 1:2 to 1:20. In this respect, weight ratios which lie within the range of from 1:2 to 1:20, but outside the range of from 10 to 50 wt.-% are not embodiments according to the invention.

Platelet-Shaped Copper-Containing Metal Pigments

The platelet-shaped copper-containing metal pigments according to the invention have an elemental copper content of at least 50 wt.-%, preferably of at least 60 wt.-%, further preferably of at least 70 wt.-%, still further preferably of at least 80 wt.-%, still further preferably of at least 90 wt.-%, in each case relative to the weight of the uncoated copper-containing metal pigment. Within the meaning of the invention, by the above-named elemental copper content is also meant the proportion of copper contained in an alloy.

According to an embodiment of the invention, the platelet-shaped copper pigments, also called copper effect pigments, preferably have a copper content of from 98 to 100 wt.-%, preferably from 99 to 99.999 wt.-%, in each case relative to the weight of the uncoated copper-containing metal pigments. It goes without saying that a person skilled in the art also reads the detail 100 wt.-% copper to include usual foreign metals possibly contained in trace amounts. The term "trace amounts" within the meaning of the present invention denotes quantities of at most 0.01 wt.-%.

According to a further preferred embodiment, the platelet-shaped copper-containing metal pigments are brass pigments containing zinc and copper which are also called gold bronzes.

In further preferred embodiments, the platelet-shaped copper-containing metal pigments are oxidized copper pigments or oxidized brass pigments. Such effect pigments are obtained by so-called "fire bronzing". The metallic effect pigments are oxidized here in a targeted manner under the action of heat. The metal oxide film that forms leads to interference effects as well as, through the reddish intrinsic color of copper oxide, to a correspondingly modified body color.

Brass effect pigments, usually called "gold bronze", preferably have a copper content of from 70 to less than 98 wt.-%, preferably 75 to 90 wt.-%, in each case relative to the weight of the uncoated copper-containing metal pigments. The zinc content accordingly preferably lies between 30 and more than 2 wt.-%, preferably at 25 to 10 wt.-%, for example at 25 wt.-%, wherein optionally up to 2 wt.-%, preferably less than 1 wt.-%, of the copper can be replaced by contaminations by other metals, in each case relative to the weight of the uncoated copper-containing metal pigment.

In the case of brass effect pigments or gold bronze effect pigments, the hue is determined by the copper-zinc ratio of the alloy.

Gold bronze effect pigments are traded commercially in characteristic natural hues, as "pale gold" with a copper proportion of approx. 90% and a remainder of approx. 10 wt.-% zinc, as "rich pale gold" with a copper proportion of approx. 85 wt.-% and a remainder of approx. 15 wt.-% zinc and as "rich gold" with a copper proportion of approx. 70 wt.-% and a remainder of approx. 30 wt.-% zinc. The detail in wt.-% relates in each case to the uncoated copper-containing metal pigment.

In a preferred embodiment, the uncoated brass effect pigments contain a "contamination" with for example 0.1 to 2 wt.-%, preferably 0.5 to 1.8 wt.-%, aluminum, in each case relative to the weight of the uncoated copper-containing metallic effect pigment. The alloys which have such a proportion of aluminum have proved to be more corrosion-stable than brass effect pigments containing exclusively copper and zinc.

In particular preferred embodiments, the platelet-shaped copper-containing uncoated metal pigments are selected from the group consisting of copper pigments, brass pigments, oxidized copper pigments, oxidized brass pigments and mixtures thereof.

Incident light is reflected, as if directed by a mirror, at the surfaces of the platelet shape of these metallic effect pigments, whereby the metallic effect, in the present case the effect of copper-containing metallic effect pigments, is brought about for an observer.

The platelet-shaped copper-containing uncoated metal pigments which are used according to the present invention have an average pigment diameter ($D_{50}$) from a range of from about 1 μm to about 200 μm, preferably from about 3 μm to 120 μm, still further preferably from about 5 μm to about 80 μm. Pigment diameters from a range of from about 10 μm to about 50 μm, preferably from about 15 μm to about 40 μm, have also proved to be very suitable.

The size distribution of the particles is preferably determined by means of laser granulometry. In this method, the particles can be measured in the form of a powder. The scattering of the irradiated laser light is detected in different spatial directions and evaluated according to the Fraunhofer diffraction theory. The particles are treated computationally as spheres. Thus, the determined diameters always relate to the equivalent spherical diameter determined over all spatial directions, irrespective of the actual shape of the particles. The evaluation of the diffraction data is the basis for a model which is aimed at the diameter of an equivalent sphere. Therefore, no absolute values are obtained, but the measured diameters have become accepted as reliable relative values in the description of the size characteristics of platelet-shaped metal pigments. The size distribution is determined, calculated in the form of a volume average relative to the equivalent spherical diameter. This volume-averaged size distribution can be represented as a total frequency distribution. The total frequency distribution is characterized in a simplified manner by different characteristic values, for example the $D_{50}$ value. The term "average pigment diameter" or "$D_{50}$" within the meaning of the present invention denotes the particle size at which 50% of the above-named particle-size distribution volume-averaged by means of laser granulometry lies below and 50% of the above-named particle-size distribution volume-averaged by means of laser granulometry lies above the given value. The measurements can be carried out for example with the particle-size analyzer HELOS from Sympatec GmbH, Clausthal-Zellerfeld, Germany.

The average thickness ($h_{50}$) of the copper-containing uncoated metallic effect pigments used in the present invention preferably lies in a range of from 25 nm to about 2 μm, preferably from about 40 nm to about 1.5 μm, still further preferably from about 70 nm to 1.1 μm, still further preferably from about 80 nm to about μm. The term "average thickness" or "$h_{50}$" within the meaning of the invention relates to the arithmetic average of the thicknesses of at least 100 metallic effect pigments by means of scanning electron microscopy (SEM). Attention is to be paid here to as good as possible an orientation of the platelets in the application medium. For this, the metallic effect pigments can be pre-treated beforehand by suitable additives. Then the cured varnish is sanded and observed in SEM after usual sample preparation of the cross-ground section. For the counting, only particles which have a good orientation are selected. The average thickness or the $h_{50}$ value relates to the uncoated copper-containing metal pigment or metallic effect pigment.

An average thickness ($h_{50}$) of from about 90 nm to about 600 nm, further preferably from about 110 nm to about 450 nm, has also proved to be very suitable.

The size-thickness ratio, which is also called the aspect ratio, preferably lies in a range of from about 1000:1 to 3:1, further preferably from about 700:1 to about 10:1, still further preferably to about 500:1 to 20:1. The term "size-thickness ratio" or "aspect ratio" within the meaning of the invention relates to the ratio of $D_{50}$ to $h_{50}$.

In particular embodiments, furthermore a size-thickness ratio of from about 450:1 to 10:1, still further preferably from about 400:1 to 15:1, has proved to be advantageous. Furthermore, it has been found in particular variants of the invention that a very suitable size-thickness ratio lies in the range of from about 80:1 to 3:1, further preferably from about 50:1 to 5:1, still further preferably from about 40:1 to 10:1.

The inventors have surprisingly discovered that an effective encapsulation of copper-containing metal pigments can be achieved if at least one enveloping metal oxide layer and at least one enveloping chemically non-reactive plastic layer are applied to the copper-containing pigments.

In specific particularly preferred embodiments, the at least one enveloping metal oxide layer is arranged between platelet-shaped copper-containing metal pigment and the at least one enveloping chemically non-reactive plastic layer. Such a layer structure has been shown to be particularly effective in respect of for example the chemicals stability and in particular the prevention of the discharge of copper ions.

In still other embodiments, on the other hand, it is preferred that the at least one chemically non-reactive plastic layer is arranged between the copper-containing metal pigment and the at least one enveloping metal oxide layer. Metal pigments with such a layer structure are characterized for example by a particular hardness.

It has moreover surprisingly been shown that metal pigments with an at least two-layered coating structure with at least one enveloping metal oxide layer and at least one enveloping chemically non-reactive plastic layer are characterized by a particular stability also vis-á-vis mechanical influences, for example abrasive influences.

Without being understood as limiting the present invention, it is assumed that the mechanical stability for example of the copper-containing metal pigments according to the invention with an external chemically non-reactive plastic layer is to be attributed to the fact that the above-named chemically non-reactive plastic layer has a degree of elasticity, i.e. is not brittle. Thus, mechanical forces which act on the copper-containing metal pigments according to the invention can be absorbed by the outer enveloping chemically non-reactive plastic layer.

Chemically Non-Reactive Plastic Layer:

By a "chemically non-reactive plastic layer" is meant according to the invention that the plastic layer is substantially completely, preferably completely, cured. This cured plastic layer therefore does not substantially react with the binder of a coating agent, such as for example a varnish, for example a powder coating, or a paint. According to a preferred variant, no reaction between the cured plastic layer and the binder of a coating agent takes place.

Thus, the "chemically non-reactive plastic layer" is certainly not a coating of not yet cured binder, such as disclosed in WO 2005/063897 A2. A binder is characterized in that it cures only later in the application, for example as a resin/hardener system or by radical polymerization.

In this case, however, the metal pigments are irreversibly incorporated into the cured powder coating. Thus, the invention makes it possible to provide a set of isolated copper-containing metal pigments which have at least one enveloping metal oxide layer and an enveloping chemically non-reactive plastic layer. In particular, the present invention makes it possible to provide powders and pastes containing the copper-containing metal pigments according to the invention.

In the case of conventional metallic effect pigments, protective layers are applied which are to protect the metallic effect pigments, usually aluminum and/or iron effect pigments, against corrosive influences from the surroundings.

In the present case, it has been shown that copper-containing pigments can be effectively encapsulated, with the result that no noticeable quantities of copper ions, preferably no copper ions, are released by the copper-containing pigments into the surroundings, for example a varnish, a paint, a plastic or a cosmetic product.

The copper-containing metal pigments according to the invention have an average thickness of the plastic layer in a range of from 100 nm to 300 nm, preferably from 120 nm to 250 nm and particularly preferably from 150 nm to 230 nm. Below an average thickness of the plastic layer of 100 nm, a clear diminution of the advantageous properties is observed. Above an average thickness of 300 nm in turn, the covering capacity and/or the luster of the metal pigments according to the invention are adversely affected in their applications.

It is assumed that these relatively thick plastic layers act above all as a barrier layer vis-á-vis water and other corrosive chemicals. Without being understood as limiting the present invention, it is the view of the inventors, however, that the layer also retains copper and/or zinc ions to a certain extent in the coating, with the result that these ions cannot enter the surrounding application medium.

In particular embodiments, it is preferred in particular that the weight proportion of the at least one chemically non-reactive plastic layer is at least 8 wt.-%, preferably at least 9 wt.-%, further preferably at least 9.5 wt.-%, more preferably at least 10 wt.-% and still more preferably at least 11 wt.-%, in each case relative to the weight of the uncoated copper-containing metal pigment.

The weight proportion of the plastic layers, relative to the weight of the uncoated copper-containing metal pigment, substantially depends on the specific surface area of the uncoated metal pigment. According to further preferred embodiments, it lies in a range of from 8 to 40 wt.-%, preferably in the range of from 9 to 35 wt.-%, further preferably in the range of from 9.5 to 30 wt.-%, more preferably in the range of from 10 to 23 wt.-% and still more preferably in the range of from 11 to 18 wt.-%, in each case relative to the weight of the uncoated copper-containing metal pigment.

According to further preferred embodiments, the at least one plastic layer substantially consists of a plastic which is selected from the group consisting of polyacrylate, polymethacrylate, polyacrylamide, polyacrylonitrile, polyvinyl chloride, polyvinyl acetate, polyamide, polyalkene, polydiene, polyalkyne, polyalkylene glycol, epoxy resin, polyester, polyether, polyol, polyurethane, polycarbonate, polyethylene terephthalate and mixtures thereof.

According to a preferred embodiment, the at least one plastic layer substantially consists of a plastic which is selected from the group consisting of polyacrylate, polymethacrylate, polyurethane, polyester and mixtures thereof. Copper-containing metallic effect pigments with at least one such plastic layer are characterized for example by an increased UV-resistance. For example, polyacrylates, polymethacrylates or mixtures thereof have proved to be particularly suitable plastics for producing plastic layers with increased UV-resistance. In particular embodiments of the invention, the at least one plastic layer therefore substantially consists of polyacrylates and/or polymethacrylates.

For example, isoamyl acrylate, lauryl acrylate, stearyl acrylate, butoxyethyl acrylate, ethoxy diethylene glycol acrylate, methoxy triethylene glycol acrylate, methoxy polyethylene glycol acrylate, methoxy dipropylene glycol acrylate, phenoxyethyl acrylate, phenoxy polyethylene glycol acrylate, tetrahydrofurfuryl acrylate, isobornyl acrylate, 2-hydroxyethyl acrylate, 2-hydroxypropyl acrylate, 2-hydroxy-3-phenoxypropyl acrylate, 2-acryloyloxyethyl succinic acid, 2-acryloyloxyethyl phthalic acid, 2-acryloyloxyethyl-2-hydroxyethyl phthalic acid, triethylene glycol diacrylate, neopentyl glycol diacrylate, 1,6-hexanediol diacrylate, 1,9-nonanediol diacrylate, dimethylol tricyclodecane diacrylate, trimethylolpropane triacrylate, pentaerythritol triacrylate, pentaerythritol tetraacrylate, dipentaerythritol hexaacrylate, 2-hydroxy-3-acryloyloxy propyl methacrylate, isooctyl acrylate, isomyristyl acrylate, isostearyl acrylate, 2-ethyl hexyl diglycol acrylate, 2-hydroxybutyl acrylate, 2-acryloyloxyethyl hexahydrophthalic acid, hydroxy pivalic acid neopentyl glycol diacrylate, polytetraethylene glycol diacrylate, ditrimethylolpropane tetraacrylate, methyl methacrylate, ethyl methacrylate, n-butyl methacrylate, isobutyl methacrylate, 2-ethylhexyl methacrylate, isodecyl methacrylate, n-lauryl methacrylate, tridecyl methacrylate, n-stearyl methacrylate, methoxydiethylene glycol methacrylate, methoxy polyethylene glycol methacrylate, cyclohexyl methacrylate, tetrahydrofurfural methacrylate, benzyl methacrylate, phenoxyethyl methacrylate, isobornyl methacrylate, 2-hydroxyethyl methacrylate, 2-hydroxypropyl methacrylate, 2-hydroxybutyl methacrylate, 2-methacryloyloxyethyl succinic acid, 2-methacryloyloxyethyl hexahydrophthalic acid, 2-methacryloyloxyethyl-2-hydroxypropyl phthalate, ethylene glycol dimethacrylate, diethylene glycol dimethacrylate, 1,4-butanediol dimethacrylate, 1,3-butanediol dimethacrylate, 1,6-hexanediol dimethacrylate, 1,9-nonanediol dimethacrylate, trimethylolpropane trimethacrylate, glycerol dimethacrylate, 2-hydroxy-3-acryloyloxy propyl methacrylate, t-butyl methacrylate, isostearyl methacrylate, methoxytriethylene glycol methacrylate, n-butoxyethyl methacrylate, 3-chloro-2-hydroxypropyl methacrylate, triethylene glycol dimethacrylate, neopentyl glycol dimethacrylate or mixtures thereof are used as monomers for producing polyacrylates and polymethacrylates.

At least one monomer with at least two, particularly preferably three, reactive double bonds (cross-linker) is particularly preferably used.

The monomer therefore particularly preferably contains or consists of 1,6-hexanediol diacrylate, 1,9-nonanediol diacrylate, dimethylol tricyclodecane diacrylate, neopentyl glycol dimethacrylate, trimethylolpropane triacrylate, trimethylolpropane trimethacrylate or mixtures thereof.

Furthermore, the acrylate-/methacrylate-containing plastic layer can additionally have acrylic acid and/or methacrylic acid as well as further radically polymerizable unsaturated compounds.

An increased UV-stability is desired when the copper-containing metal pigments according to the invention, in particular copper-containing metallic effect pigments, are used in external applications, such as for example in a car paint, a façade paint, etc.

According to a further variant according to the invention, the plastic layer is selected from the group consisting of polyamide, polycarbonate, polyvinyl chloride, polyethylene terephthalate and mixtures thereof. Copper-containing metal pigments with at least one such plastic layer are characterized for example by an increased temperature stability.

According to a preferred embodiment of the invention, the plastic is temperature-stable up to a temperature of at least 180° C., further preferably of at least 260° C., still further preferably up to a temperature of at least 350° C. By temperature-stable is meant that the plastic coating of the platelet-shaped copper-containing metal pigments does not melt and/or break down at the above-named temperature. A possible melting and/or break-down at a given temperature can be tested for example by means of dynamic differential calorimetry.

According to a further preferred embodiment, physically bonded surface modifiers are applied to the enveloping chemically non-reactive plastic layer.

Metal Oxide Layer:

According to a preferred variant of the invention, the at least one metal oxide layer is selected from the group consisting of silicon oxide, aluminum oxide, boron oxide, zirconium oxide, cerium oxide, iron oxide, titanium oxide, chromium oxide, tin oxide, molybdenum oxide, oxide hydrates thereof, hydroxides thereof and mixtures thereof. In particular preferred embodiments, the at least one metal oxide layer is characterized in that the at least one metal oxide layer substantially consists of silicon oxide.

Within the framework of this invention, by the term "substantially consisting of silicon oxide" is meant that the layer consists predominantly of silicon oxide, preferably $SiO_2$, but can also contain up to 20 wt.-% water, relative to the silicon oxide layer. Furthermore, in a sol-gel synthesis from tetraalkoxysilanes, the silicon oxide can contain up to 5 wt.-% alkoxy groups which have not been hydrolyzed and condensed.

At least one, preferably all, of the at least one enveloping metal oxide layers preferably consists/consist of a silicon oxide layer or silicon oxide layers, preferably an $SiO_2$ layer or $SiO_2$ layers, and/or aluminum oxide layer or aluminum oxide layers, preferably an $Al_2O_3$ layer or $Al_2O_3$ layers. In particular preferred embodiments, at least one, preferably all, of the at least one enveloping metal oxide layers consists/consist of a silicon oxide layer(s), preferably an $SiO_2$ layer. In further particular preferred embodiments, at least one, preferably all, of the at least one enveloping metal oxide layers consists or consist of an aluminum oxide layer or aluminum oxide layers, preferably an $Al_2O_3$ layer or $Al_2O_3$ layers. In specific particularly preferred embodiments, the at least one enveloping metal oxide layer is one (1) silicon oxide layer, preferably one (1) $SiO_2$ layer.

It has surprisingly been shown that the use of a particular minimum quantity of metal oxide layer is advantageous in order to achieve for example a particularly high oxidation stability. In particular embodiments, it is therefore preferred that the weight proportion of the at least one metal oxide layer is at least 0.9 wt.-%, preferably at least 1.0 wt.-%, more preferably at least 1.5 wt.-%, still more preferably at least 2.0 wt.-% and most preferably at least 2.5 wt.-%, in each case relative to the weight of the uncoated copper-containing metal pigment.

According to a further preferred embodiment of the invention, the weight proportion of the metal oxide layer lies in a range of from 0.9 to 12 wt.-%, further preferably from 1 to 10 wt.-%, and particularly preferably from 1.5 to 9 wt.-% and quite particularly preferably from 2 to 8 wt.-%, in each case relative to the weight of the uncoated copper-containing metal pigment.

In addition, it was surprisingly found that in the case of platelet-shaped copper-containing metal pigments in which a metal oxide layer according to the invention was applied as the top layer, it is particularly advantageous to apply a larger quantity of the metal oxide layer. In particular embodiments, therefore, it is preferred that the weight proportion of the at least one metal oxide layer in platelet-shaped copper-containing metal pigments in which a metal oxide layer according to the invention was applied as the top layer is at least 0.9 wt.-%, relative to the weight of the uncoated copper-containing metal pigment. In particular embodiments, it is preferred in particular that the weight proportion of the at least one metal oxide layer in platelet-shaped copper-containing metal pigments in which a metal oxide layer according to the invention was applied as the top layer is at least 1.0 wt.-% and in platelet-shaped copper-containing metal pigments in which a chemically non-reactive plastic layer according to the invention was applied as the top layer is at least 0.9 wt.-%; preferably in platelet-shaped copper-containing metal pigments in which a metal oxide layer according to the invention was applied as the top layer is at least 1.5 wt.-% and in platelet-shaped copper-containing metal pigments in which a chemically non-reactive plastic layer according to the invention was applied as the top layer is at least 1.0 wt.-%; more preferably in platelet-shaped copper-containing metal pigments in which a metal oxide layer according to the invention was applied as the top layer is at least 2.0 wt.-% and in platelet-shaped copper-containing metal pigments in which a chemically non-reactive plastic layer according to the invention was applied as the top layer is at least 1.5 wt.-%; and still more preferably in platelet-shaped copper-containing metal pigments in which a metal oxide layer according to the invention was applied as the top layer is at least 2.5 wt.-% and in platelet-shaped copper-containing metal pigments in which a chemically non-reactive plastic layer according to the invention was applied as the top layer is at least 2.0 wt.-%, in each case relative to the weight of the uncoated copper-containing metal pigment. Without being understood as limiting the present invention, it is the view of the inventors that a larger quantity of metal oxide is necessary to form an external metal oxide layer which is sufficiently resistant for example to mechanical influences and provides the desired stabilization of the metal pigment. In particular embodiments, it is preferred in particular that the weight proportion of the at least one enveloping metal oxide layer in platelet-shaped copper-containing metal pigments in which a chemically non-reactive plastic layer forms the top layer of the coating lies in a range of from 0.9 to 12 wt.-% and in platelet-shaped copper-containing metal pigments in which a metal oxide layer forms the top layer of the coating lies in a range of from 1.0 to 10 wt.-%, preferably in platelet-shaped copper-containing metal pigments in which a chemically non-reactive plastic layer forms the top layer of the coating lies in a range of from 1.0 to 10 wt.-% and in platelet-shaped copper-containing metal pigments in which a metal oxide layer forms the top layer of the coating lies in a range of from 1.5 to 9 wt.-%, more preferably in platelet-shaped copper-containing metal pigments in which a chemically non-reactive plastic layer forms the top layer of the coating lies in a range of from 1.5 to 9 wt.-% and in platelet-shaped copper-containing metal pigments in which a metal oxide layer forms the top layer of the coating lies in a range of from 2.0 to 8 wt.-% and still more preferably in platelet-shaped copper-containing metal pigments in which a chemically non-reactive plastic layer forms the top layer of the coating lies in a range of from 2.0 to 8 wt.-% and in platelet-shaped copper-containing metal pigments in which a metal oxide layer forms the top layer of the coating lies in a range of from 2.5 to 7 wt.-%, in each case relative to the weight of the uncoated copper-containing metal pigment.

The average thickness of the metal oxide layer preferably lies in a range of from 2 nm to 25 nm, further preferably from 3 nm to 20 nm. An average thickness in a range of from 5 nm to 10 nm has also proved to be very suitable.

Surprisingly, in the platelet-shaped copper-containing metal pigment according to the invention, one (1) thin metal oxide layer in conjunction with one (1) chemically non-reactive plastic layer already suffices on the one hand to protect the copper-containing metal pigments from environmental influences and on the other hand to prevent copper ions from being released by the copper-containing metal pigment into the surroundings, for example a varnish, a paint, a cosmetic product, etc.

In a very preferred embodiment, the metal oxide layer is applied directly to the metal substrate as a first layer. In particular in this embodiment it is assumed that the metal oxide layer as a start represents a relatively effective barrier against copper and/or zinc ions being discharged. Those metal ions that still overcome this barrier are obviously effectively trapped in the plastic layer.

Synergistic Action of the Two Layers:

It is assumed that the enveloping metal oxide layer and the enveloping chemically non-reactive plastic layer interact in a synergistic manner.

Firstly, it is assumed that the enveloping chemically non-reactive plastic layer, i.e. the substantially completely polymerized, preferably polymerized, and/or cured plastic layer forms a plastic matrix so dense that any copper ions getting through the $SiO_2$ layer are reliably incorporated by the dense plastic layer.

Secondly, it is assumed that any corrosive substances getting through the chemically non-reactive plastic layer from the surroundings of the copper-containing metal pigment according to the invention, such as e.g. $H^+$ or $OH^-$ ions, are also trapped between the metal oxide layer and plastic layer, with the result that these corrosive substances come into contact with the copper-containing metal pigments only slightly, preferably not at all. Any copper ions nevertheless released by corrosive influences are then, as already stated above, presumably trapped between the metal oxide layer and the chemically non-reactive plastic layer and therefore not released to the surroundings, for example a paint or a varnish.

Thus, the at least two-layered coating structure interacts synergistically with an enveloping metal oxide layer and an enveloping chemically non-reactive plastic layer, with the result that any corrosive influences from the surroundings, for example when the copper-containing pigments are used in a car paint, a façade paint, etc., do not come into contact with copper and, should this have happened, any copper ions released do not enter the surroundings.

A further important aspect is the oxidation of the platelet-shaped copper-containing metal pigments with atmospheric oxygen at temperatures above approx. 80° C. This occurs for example both during the curing of powder coating (baking temperatures approx. 200° C.) or during coil-coating varnishing (baking temperatures approx. 280° C.). Here, it has surprisingly been shown that a thin metal oxide layer combined with the chemically non-reactive plastic layer already suffices to prevent an oxidation of the copper-containing metal pigment. Although the plastic layer is oxygen-permeable, it gives the product the necessary chemicals stability.

In particular embodiments, it is preferred in particular that the sum of the amount of the polymer layer and the amount of the metal oxide layer lies in a range of from 13 to 40 wt.-%, preferably in a range of from 14 to 35 wt.-%, more preferably in a range of from 15 to 33 wt.-%, still more preferably in a range of from 16 to 29 wt.-%, in each case relative to the weight of the uncoated metal pigment.

It is preferred according to the invention to keep the sum of the amount of the polymer layer and the amount of the metal oxide layer as low as possible overall. In this way, an optimum covering capacity of the metallic effect pigments is guaranteed. In addition it has been shown that, if the layers are too thick, the metallic effect pigments can tend to agglomerate. Furthermore, in the case of thicker layers which are above 50 wt.-%, relative to the weight of the uncoated metal pigment, the protective action surprisingly decreases. It is assumed that thicker layers have a low quality with respect to their protective properties, because they are more brittle.

It is essential to the invention that the chemically non-reactive plastic layer is applied in a much higher proportion by weight relative to the metal oxide layer.

Particularly preferred embodiments have a weight ratio of the at least one metal oxide layer to the at least one chemically non-reactive plastic layer in a range of from 1:2.2 to 1:17, preferably in a range of from 1:2.5 to 1:15, further preferably in a range of from 1:2.7 to 1:13 and still further preferably in a range of from 1:3 to 1:10.

Furthermore, it has surprisingly been shown that it is advantageous in particular variants to choose a more narrow range of the weight ratio of the at least one metal oxide layer to the at least one chemically non-reactive plastic layer in platelet-shaped copper-containing metal pigments in which a chemically non-reactive plastic layer according to the invention was applied as the first layer. In particular embodiments, it is therefore preferred that the weight ratio of the at least one metal oxide layer to the at least one chemically non-reactive plastic layer in platelet-shaped copper-containing metal pigments in which a chemically non-reactive plastic layer according to the invention was applied as the first layer lies in a range of from 1:2.2 to 1:17 and in platelet-shaped copper-containing metal pigments in which a metal oxide layer according to the invention was applied as the first layer lies in a range of from 1:2.0 to 1:20; preferably in platelet-shaped copper-containing metal pigments in which a chemically non-reactive plastic layer according to the invention was applied as the first layer lies in a range of from 1:2.5 to 1:15 and in platelet-shaped copper-containing metal pigments in which a metal oxide layer according to the invention was applied as the first layer lies in a range of from 1:2.2 to 1:17; further preferably in platelet-shaped copper-containing metal pigments in which a chemically non-reactive plastic layer according to the invention was applied as the first layer lies in a range of from 1:2.7 to 1:13 and in platelet-shaped copper-containing metal pigments in which a metal oxide layer according to the invention was applied as the first layer lies in a range of from 1:2.5 to 1:15; and still further preferably in platelet-shaped copper-containing metal pigments in which a chemically non-reactive plastic layer according to the invention was applied as the first layer lies in a range of from 1:3 to 1:10 and in platelet-shaped copper-containing metal pigments in which a metal oxide layer according to the invention was applied as the first layer lies in a range of from 1:2.7 to 1:13. Without being understood as limiting the invention, it is the view of the inventors that a chemically non-reactive plastic layer applied first of all provides a more irregular surface for subsequent coatings, with the result that the use of a more precisely specified weight ratio of the at least one metal oxide layer to the at least one chemically non-reactive plastic layer in platelet-shaped copper-containing metal pigments in which a chemically non-reactive plastic layer according to the invention was applied as the first layer proves to be advantageous in order to bring about the effects according to the invention in a particularly pronounced form.

In particular variants of the invention, ranges are preferred in particular which are characterized by a quantity of plastic of from 8 wt.-% to 40 wt.-% and a quantity of metal oxide of from 0.9 wt.-% to 12 wt.-%, preferably a quantity of plastic of from 9 wt.-% to 35 wt.-% and a quantity of metal oxide of from 1 wt.-% to 10 wt.-%, further preferably a quantity of plastic of from 10 wt.-% to 30 wt.-% and a quantity of metal oxide of from 1.5 wt.-% to 9 wt.-%, still further preferably a quantity of plastic of from 12 wt.-% to 25 wt.-% and a quantity of metal oxide of from 2 wt.-% to 8 wt.-%, in each case relative to the weight of the uncoated copper-containing metal pigment.

In specifically preferred embodiments, the at least one chemically non-reactive plastic layer substantially consists of polyacrylate and/or polymethacrylate and the at least one metal oxide layer substantially consists of silicon oxide, preferably $SiO_2$, wherein the weight ratio of the at least one metal oxide layer to the at least one chemically non-reactive plastic layer lies in a range of from 1:2.2 to 1:17 and the sum of the amount of the at least one chemically non-reactive plastic layer and the amount of the at least one metal oxide layer lies in a range of from 10 to 50 wt.-%, relative to the weight of the uncoated metal pigment.

In further specific preferred embodiments, the at least one chemically non-reactive plastic layer substantially consists of polyacrylate and/or polymethacrylate and the at least one metal oxide layer substantially consists of silicon oxide, preferably $SiO_2$, wherein the weight ratio of the at least one metal oxide layer to the at least one chemically non-reactive plastic layer lies in a range of from 1:2.5 to 1:15 and the sum of the amount of the at least one chemically non-reactive plastic layer and the amount of the at least one metal oxide layer lies in a range of from 13 to 40 wt.-%, relative to the weight of the uncoated metal pigment.

In further specific preferred embodiments, the at least one chemically non-reactive plastic layer substantially consists of polyacrylate and/or polymethacrylate and the at least one metal oxide layer substantially consists of silicon oxide, preferably $SiO_2$, wherein the weight ratio of the at least one metal oxide layer to the at least one chemically non-reactive plastic layer lies in a range of from 1:2.2 to 1:17 and the sum of the amount of the chemically non-reactive plastic layer and the amount of the metal oxide layer lies in a range of from 13 to 40 wt.-%, relative to the weight of the uncoated metal pigment. In particular ones of the above-named specific preferred embodiments, the weight ratio of the at least one metal oxide layer to the at least one plastic layer lies in a range of from 1:2.5 to 1:15.

In further specific preferred embodiments, the weight ratio of the at least one metal oxide layer to the at least one chemically non-reactive plastic layer lies in a range of from 1:2.5 to 1:15.

In further preferred embodiments, the above-named specific preferred embodiments are supplemented by the fact that the proportion by weight of the silicon oxide, preferably $SiO_2$, layer lies in a range of from 1.5 to 9 wt.-%, relative to the weight of the uncoated copper-containing metal pigment.

In further preferred embodiments, the above-named specific preferred embodiments are supplemented by the fact that the proportion by weight of the at least one chemically non-reactive plastic layer lies in a range of from 10 to 35 wt.-%, relative to the weight of the uncoated copper-containing metal pigment.

Optionally, one or more organofunctional silanes which contain at least one radically polymerizable double bond, preferably at least one acrylate and/or methacrylate group, can be applied between the SiO$_2$ layer and the plastic layer.

The copper-containing metal pigments according to the invention have two important advantages as a result of the relatively low thicknesses of the metal oxide layer and the relatively high plastic layer thickness.

Firstly, the covering capacity, i.e. the surface area covered per weight unit of pigment according to the invention, is still very good, compared with the covering of an uncoated metal pigment. The thicker the applied transparent coating is, the worse the covering capacity becomes, because ever fewer metal particles are present per gram of pigment. The covering capacity can additionally be made worse if more fines of the metal pigments are incorporated into the coating of larger pigments as the coating thickness increases. However, these fines are critical for a good covering capacity.

In this respect, it is advantageous if the coating has as small a layer thickness as possible, because then fewer fines are incorporated into the coating of larger pigments and these can thus still contribute to the covering through a statistical distribution in the varnish. In order to be able to keep the average layer thickness of the coating low, it is a prerequisite that the applied enveloping transparent coating effectively protects the copper-containing metal pigment from corrosive environmental influences and also prevents copper ions from being released into the surroundings.

A combination of a thin metal oxide layer with a chemically non-reactive plastic layer surprisingly makes it possible both to protect the copper-containing metal pigment from corrosive environmental influences and to effectively encapsulate the copper ions so that they are not released into the surroundings. With regard to the transparent coating with low layer thickness, the copper-containing metal pigments according to the invention therefore have an excellent covering capacity.

In particular embodiments, the at least one plastic layer is obtained by means of an initiator-induced radical polymerization. It has surprisingly been shown that, in the case of a radical polymerization started by an initiator, a coarse chemically non-reactive plastic layer is obtained. This is very advantageous if the platelet-shaped copper-containing metal pigments according to the invention are used in a powder coating. The behavior is obviously such that a coarser surface structure of the chemically non-reactive plastic layer effects an easier electrostatic chargeability of the platelet-shaped copper-containing metal pigments according to the invention. In the case of a stronger electrostatic charge, the platelet-shaped copper-containing metal pigments according to the invention can be applied more easily to a workpiece to be varnished.

This leads, on the one hand, to a more effective varnishing in which the proportion of powder coating not applied, the so-called overspray, is reduced. On the other hand, workpieces to be varnished can be provided with a higher-quality powder coating varnishing within a shorter time.

In contrast to uses of the metallic effect pigments according to the invention in powder coating, it has been shown that smooth surfaces, such as form in the case of thermal polymerization, are advantageous for wet coating uses such as coil coating. Due to the smooth surfaces, there is a uniform passage of the light through the varnish-coating boundary layer of the pigment. Undesired scattering effects are thereby minimized, with the result that these pigments appear more brilliant than comparable metallic effect pigments from the state of the art. A further advantage is that, due to the smaller surface, less binder is needed to wet the pigments, with the result that higher pigment loads are possible.

Further Layers:

One or more further layers can be arranged between the at least one enveloping metal oxide layer and the at least one enveloping chemically non-reactive plastic layer. These one or more additional layers can also be for example additional metal oxide layers. In particular embodiments, however, it is preferred that the possibly present layers between the at least one enveloping metal oxide layer and the at least one enveloping chemically non-reactive plastic layer do not represent a metal oxide layer or plastic layer within the meaning of the present invention.

In a preferred embodiment, however, organofunctional silanes, titanates, aluminates, phosphonic acids (e.g. VPS: vinyl phosphonic acid), phosphoric acid esters and/or zirconates are used here as adhesion promoter and/or further layer component, wherein organofunctional silanes are particularly preferred. These compounds can bind for example particularly well to the metal surface or metal oxide surface because of their known hydrolysis and condensation reactions. The compounds should have at least one chemically polymerizable group which is preferably adapted to the plastic layer.

If the plastic layer consists for example of polyacrylates and/or polymethacrylates, the organofunctional silane preferably has at least one functional group which can be chemically reacted with an acrylate group and/or methacrylate group of polyacrylate and/or polymethacrylate. Radically polymerizable organic functional groups have proved to be very suitable. Preferably, the at least one functional group is selected from the group which consists of acryl, methacryl, vinyl, allyl, ethinyl as well as further organic groups with unsaturated functions.

Preferably, the organofunctional silane has at least one acrylate and/or methacrylate group, because these can be reacted with the acrylate or methacrylate compounds used to produce the polyacrylate and/or polymethacrylate completely problem-free, accompanied by the formation of a homogeneous plastic layer.

According to the invention, for example (methacryloxymethyl)methyldimethoxysilane, methacryloxymethyltrimethoxysilane, (methacryloxymethyl)methyldiethoxysilane, methacryloxymethyltriethoxysilane, 2-acryloxyethylmethyldimethoxysilane, 2-methacryloxyethyltrimethoxysilane, 3-acryloxypropylmethyldimethoxysilane, 2-acryloxyethyltrimethoxysilane, 2-methacryloxyethyltriethoxysilane, 3-acryloxypropyltrimethoxysilane, 3-acryloxypropyltripropoxysilane, 3-methacryloxypropyltriethoxysilane, 3-methacryloxypropyltrimethoxysilane, 3-methacryloxypropyltriacetoxysilane, 3-methacryloxypropylmethyldimethoxysilane, vinyltrichlorosilane, vinyl trimethoxysilane vinyldimethoxymethylsilane, vinyltriethoxysilane, vinyltris(2-methoxyethoxy)silane, vinyltriacetoxysilane or mixtures thereof can be used as organofunctional silanes containing an acrylate and/or methacrylate.

Such silanes can act as adhesion promoters between metal oxide layer and plastic layer or between metal oxide layer, preferably silicon oxide layer, and plastic layer. In other embodiments, such silanes can also be at least partially incorporated by polymerization into the plastic layer, as described in WO 2008/095697 A1, which is included herewith by reference.

Within the framework of this invention, by a chemically non-reactive plastic layer which "substantially consists of polyacrylate and/or polymethacrylate" is meant that such a layer can be modified by acrylate- and/or methacrylate-containing silanes. The proportion of the quantities of the acrylate- and/or methacrylate-containing silanes used corresponds at most to the proportion of the quantities of the acrylate and/or methacrylate monomers used. The molar ratio of acrylate- and/or methacrylate-containing silanes to acrylate and/or methacrylate monomers is preferably from 1:2 to 1:40, preferably from 1:3 to 1:30.

However, layers in which the acrylate- and/or methacrylate-containing silanes are incorporated into the at least one metal oxide layer, preferably silicon oxide layer, during a sol-gel process are not a subject of this invention. Such layers are described in EP 1812519 B1. It has been shown that, using the technology described there, the layers cannot be produced in a reliably reproducible manner, in order to give the copper-containing platelet-shaped metal pigments the necessary stabilities.

One or more further layers can also be arranged between the copper-containing metal pigments and the at least one enveloping metal oxide layer as well as the at least one chemically non-reactive plastic layer. For example, a layer of copper oxide can be arranged between the enveloping metal oxide layer and the copper-containing metal pigments. This copper oxide layer can be obtained for example by so-called fire-coloring in which copper-containing pigments are heated in the presence of atmospheric oxygen, accompanied by the formation of a colored copper oxide layer. However, this oxidation must take place before the application of the metal oxide layer, because the metal oxide layer prevents the oxidation. Because of the intrinsic color and because of interference effects, these copper oxide layers produce widely different hues in the yellow-red color spectrum depending on their layer thicknesses in the case of platelet-shaped metallic effect pigments.

In the so-called fire treatment of copper-containing metallic effect pigments, atmospheric oxygen acts on the copper-containing metallic effect pigment over a defined period at a defined temperature, whereby a thin copper oxide layer forms on the copper-containing metal platelet. Interesting shades are brought about by interference reflection. Fire-colored copper-containing metallic effect pigments are traded commercially inter alia in the hues English Green, Lemon, Deep Gold and in Fire red colors. The fire-colored platelet-shaped, copper-containing metal pigments, which are also called copper-containing metallic effect pigments, are already protected against corrosion or corrosive influences to a certain extent because of the copper oxide layer produced by the heat treatment in the presence of atmospheric oxygen.

The copper-containing metal pigment or the copper-containing metal pigment provided with a copper oxide layer by fire-coloring then has at least one enveloping metal oxide layer which is different from copper oxide. The at least one enveloping metal oxide layer which interacts synergistically with the chemically non-reactive plastic layer therefore is not a copper oxide layer within the meaning of the invention.

According to a preferred variant of the invention, the at least one metal oxide layer which interacts synergistically with the at least one chemically non-reactive plastic layer is not the oxidation product of the uncoated copper-containing metal pigment. The metal oxide layer which interacts synergistically with the at least one chemically non-reactive plastic layer is preferably applied in a separate step. The separate step can be for example a wet-chemical coating or a gas-phase coating, for example by means of PVD or CVD.

In particular very preferred embodiments of the invention, the enveloping metal oxide layer(s) and the enveloping chemically non-reactive plastic layer(s) follow one another directly. In further particular, very preferred embodiments, it is furthermore preferred that the enveloping metal oxide layer or the enveloping chemically non-reactive plastic layer are applied directly to the copper-containing metal pigment surface or directly to the copper oxide layer.

In particular preferred embodiments, the copper-containing metal pigments have, in addition to an optional copper oxide layer, only one (1) enveloping metal oxide layer and only one (1) enveloping chemically non-reactive plastic layer.

Determining Layer Thicknesses and Amount of Plastic Layer and Metal Oxide Layer

The layer thicknesses of the metal oxide layers and of the plastic layers on the copper-containing metal pigments are determined for example by means of SEM pictures on suitable cross-ground sections. Here, the pigments are applied in a varnish and this is cured. Attention is to be paid here to as good as possible an orientation of the platelets in the application medium. For this, the metallic effect pigments can be pre-treated beforehand by suitable additives. Then the cured varnish is sanded and observed in SEM after usual sample preparation of the cross-ground section. For the counting, only particles which have a good orientation are selected. In this method, poorly-oriented platelets yield a high error because of the unknown viewing angle. The coatings have a very good contrast to the metal core. Should it be impossible to distinguish well between the layer thicknesses of the metal oxide layer and the plastic layer, locally resolved EDX analyses can be used before the layer thicknesses are measured. The term "average layer thickness" within the meaning of the invention denotes the arithmetic average of the layer thicknesses of the layers of at least 20 metal pigments. If the coating is irregular, the arithmetic average of the thinnest and of the thickest points of the coating of the respective particle is generated. Individual serious deviations which affect for example the incorporation of already coated finely dispersed pigments into the coating are not taken into consideration in the calculation of the average layer thickness.

The amount of metal oxide can take place via an elemental analysis. Thus, for example in the case of an $SiO_2$ layer, the Si content can be determined in relation to the amount of the copper-containing metal used as substrate and then projected onto $SiO_2$.

Producing Metallic Effect Pigments:

Preferably, the uncoated platelet-shaped copper-containing metal pigments are obtained by grinding copper-containing grit, for example copper or brass grit.

In the case of copper grit, highly pure, electrolytically obtained copper is preferably used. Where necessary, the copper grit is screened in order to obtain a desired size distribution.

The copper-containing grit, for example brass grit, can have a size distribution with a $D_{grit,50}$ of from 1 to 220 µm and a $D_{grit,90}$ of from 2 to 470 µm. Such a grit is preferably used in a dry grinding. The copper-containing grit, e.g. brass grit, can also be converted to platelet-shaped copper-containing pigments by wet grinding. After the grinding, a screening may be necessary in order to obtain the desired uncoated platelet-shaped, copper-containing metal pigment fraction.

The copper-containing metal grit can also contain zinc and/or aluminum as well as further metals, in addition to copper. For example, brass can contain 0.1 to 2 wt.-% aluminum, relative to the weight of the uncoated copper-containing metal pigment.

In the case of brass grit, highly pure electrolytically obtained copper and zinc are preferably used and preferably alloyed by the addition of a little aluminum, as stated above, as reducing agent. For this, copper and zinc are fused together and the produced brass melt is atomized or nebulized into a brass grit. The thus-obtained brass grit can then be screened, for example using a cyclone, in order to obtain a starting brass grit with a desired size distribution.

The brass grit preferably has a size distribution with a $D_{grit,50}$ in the range of from 1 to 220 µm, preferably from 2 µm to 190 µm, more preferably from 4 to 150 µm and still more preferably from 6 µm to 110 µm, and a $D_{grit,90}$ of from 2 to 470 µm, preferably from 3 µm to 410 µm, more preferably from 6 to 360 µm and still more preferably from 12 to 310 µm.

The copper-containing metal grit with the desired size distribution is subsequently ground to uncoated platelet-shaped copper-containing metallic effect pigments.

The grinding of copper-containing metal grit, for example copper or brass grit, takes place predominantly according to the Hametag dry grinding process. Here, the copper-containing metal grit, for example copper or brass grit, is ground in ball mills in several grinding steps under different grinding conditions, such as for example mill size, mill diameter, rotational speed of the mill, ball size, grinding duration, with the addition of lubricant, such as for example stearic or oleic acid, to prevent cold welding of the copper-containing metal particles, for example copper or brass particles, and with grinding bodies, such as e.g. steel balls. The uncoated platelet-shaped copper-containing metallic effect pigments are collected in different containers after the grinding and optional screening and then homogenized or mixed.

In a wet grinding of copper-containing metal grit, for example copper or brass grit, this is ground in the presence of lubricant and solvent. A wet grinding is preferred, because this is gentler than a dry grinding.

In particular preferred embodiments, the uncoated platelet-shaped copper-containing metal pigments have, according to a thickness computation using scanning electron microscopy (SEM), an $h_{50}$ value in a range of from 10 to 50 nm, preferably from 15 to 45 nm, particularly preferably from 15 to 40 nm and quite particularly preferably from 20 to 35 nm.

Furthermore, in particular embodiments, the uncoated platelet-shaped copper-containing metallic effect pigments have a thickness distribution determined via thickness computation using scanning electron microscopy (SEM) with an $h_{90}$ value of from 20 to 70 nm, preferably from 20 to 60 nm, further preferably from 21 to 50 nm and particularly preferably from 22 to 40 nm.

In a furthermore preferred embodiment of the invention, the uncoated platelet-shaped copper-containing metallic effect pigments have an $h_{10}$ value of the thickness distribution in the range of from 8 to 25 nm and particularly preferably from 10 to 20 nm.

Furthermore, in particular preferred embodiments, the uncoated platelet-shaped copper-containing metallic effect pigments have a relative width of the thickness distribution $\Delta h$ determined via thickness computation using scanning electron microscopy (SEM) which is calculated using the corresponding cumulative breakthrough curve of the relative frequency according to the formula $$\Delta h = (h_{90} - h_{10})/h_{50}$$

of from 0.3 to 0.9, preferably from 0.35 to 0.85 and particularly preferably from 0.4 to 0.8.

Furthermore, the uncoated platelet-shaped copper-containing metallic effect pigments in particular preferred embodiments have an aspect ratio of from 150 to 3,000. Preferably, the uncoated platelet-shaped copper-containing pigments are characterized by an aspect ratio of from 250 to 2,500, further preferably from 300 to 1,000 and particularly preferably from 325 to 600.

Further information on a grinding process that can be used here is found in WO 2009/152941 A2, reference to the complete disclosure content of which is made herewith.

In a further preferred embodiment, the copper-containing grit particles, for example copper or brass particles, are ground in two stages. The copper-containing grit particles, for example copper or brass particles, are pre-deformed in the first stage and ground in the second stage until the completely two-dimensionally deformed uncoated platelet-shaped copper-containing metallic effect pigments are obtained.

According to a further preferred variant of the invention, uncoated copper effect pigments or uncoated brass effect pigments obtained by physical vapor deposition, which are also called PVD copper effect pigments or PVD brass effect pigments below, can also be used. Such effect pigments are disclosed for example in EP 1 529 0784 B1 and EP 1 529 0785 B1.

PVD copper effect pigments or PVD brass effect pigments have an absolutely flat surface. In this case, a coarse surface cannot be produced by coating with metal oxide and a chemically non-reactive plastic layer. These uncoated platelet-shaped copper-containing metallic effect pigments according to the invention produced using PVD copper effect pigments or PVD brass effect pigments, after coating with the two-layered coating according to the present invention, nevertheless have an excellent resistance to corrosive influences from the surroundings and prevent copper ions from being released into the surroundings.

Platelet-shaped copper-containing metal pigments according to the invention prepared using PVD copper effect pigments or PVD brass effect pigments are suitable with regard to the smooth surface in particular for use in paints, printer inks, varnishes and cosmetics. A use of the PVD copper effect pigments or PVD brass effect pigments coated according to the invention in powder coatings is less preferred.

Uses

Cosmetics

In cosmetic formulations, the platelet-shaped copper-containing metal pigments according to the invention can be combined with raw materials, auxiliary materials and active ingredients suitable for the respective use. The concentration of the platelet-shaped copper-containing metal pigments in the formulation can lie between 0.001 wt.-% for rinse-off products and 40.0 wt.-% for leave-on products.

The platelet-shaped copper-containing metal pigments according to the invention are suitable in particular for use in cosmetics, such as e.g. body powder, face powder, pressed and loose powder, face makeup, powder cream, cream makeup, emulsion makeup, wax makeup, foundation, mousse makeup, blusher, eye makeup such as eyeshadow, mascara, eyeliner, liquid eyeliner, eyebrow pencil, lip balm, lipstick, lip gloss, lip liner, hair styling compositions such as hair spray, hair mousse, hair gel, hair wax, hair mascara, permanent or semi-permanent hair dyes, temporary hair dyes, skin care compositions such as lotions, gels, emulsions as well as nail polish compositions.

To achieve specific color effects, further coloring agents and/or conventional effect pigments or mixtures thereof in variable quantity ratios can be used in the cosmetic applications in addition to the platelet-shaped copper-containing metal pigments according to the invention. For example, pearlescent pigments customary in the trade based on natural mica coated with highly refractive metal oxides (such as e.g. the Prestige product group from Eckart), BiOCl platelets, $TiO_2$ platelets, pearlescent pigments based on synthetic mica coated with highly refractive metal oxides or based on glass platelets coated with highly refractive metal oxides (such as e.g. the MIRAGE product group from Eckart), $Al_2O_3$, $SiO_2$ or $TiO_2$ platelets can be used as conventional effect pigments. In addition, metallic effect pigments, such as e.g. the Visionaire product group from Eckart, can also be added. The coloring agents can be selected from inorganic or organic pigments.

Coating Agent

The object on which the invention is based is furthermore achieved by providing a coating agent which contains platelet-shaped copper-containing metal pigments according to the invention.

According to a preferred variant of the present invention, the coating agent is a varnish, such as e.g. a coil-coating varnish, a varnish concentrate, a printer ink, a printer ink concentrate, a paint, a paint concentrate, a powder coating or a powder coating concentrate.

In the above-named coating agents, it is very advantageous that the platelet-shaped copper-containing metal pigments according to the invention release no noticeable quantities of copper ions, preferably no copper ions, to the coating agent.

As stated at the outset, if copper ions are released to a coating agent, there is the problem on the one hand that reduction reactions result when copper(I) changes into the oxidation state copper(II). On the other hand there is the problem that copper(II) ions form colored complexes, for example strongly blue-colored complexes with amines.

Naturally, such a discoloration of coating agents is undesired.

The object on which the invention is based is furthermore achieved by providing a coated object, wherein the coated object contains or has platelet-shaped copper-containing pigments according to the invention or a coating agent according to the invention.

The coated objects can be car bodyworks, façade elements, printed matter, such as for example printed films, paper, cardboard boxes, plastic shaped parts, etc.

The object on which the invention is based is furthermore achieved by the use of the platelet-shaped copper-containing metal pigments according to the invention in a coating agent.

The copper-containing metal pigments according to the invention have proved to be very advantageous for example in paints and varnishes based on organic solvents or water. As a result of their outstanding stability, they have proved to be particularly suitable for applications in which for example a color stability lasting years or decades under burdensome conditions is necessary. For example, the pigments according to the invention are well-suited to applications in which there is skin contact, and external applications. Thus, for example, façade elements or mobile phone shells can be colored with them.

In organic-based paints and varnishes, the pigments according to the invention have proved to be very advantageous, because for example an excellent long-term stability could be achieved with them. This appears to be attributable to the reliable inclusion of the copper ions, whereby undesired reactions of the varnish constituents are avoided. However, use in water-based paints and varnishes has also proved to be very advantageous, in which a reliable coloring with long-term stability was achieved. It is assumed that the particularly good water stability of the copper-containing metal pigments according to the invention prevents a reaction of the copper with the water, and thus a color change, in the long term. The copper-containing metal pigments according to the invention are therefore particularly well-suited for example to use in aqueous dispersion paints such as wall paints. In particular, forms of use such as application as a wall paint also profit from the long-term stability in their applied form. Thus, for example, no greenish or bluish discoloration as a result of copper ions being discharged is observed even in the case of moist walls.

Preferred coating agents containing the platelet-shaped copper-containing metal pigments according to the invention are water varnishes, powder coatings, nail polishes, polymers and coil-coating formulations. In particular preferred embodiments, the coating agent is a powder coating, a nail polish composition or a varnish for use in the coil-coating process.

Powder Coating

Powder coatings are used for example in industrial series production for coating electrically conductive and temperature-resistant materials. The powder coating to be applied is present here as a solid and solvent-free powder. Furthermore, the powder coatings used as base coat or one-coat paint are almost completely recyclable. The environmentally friendly and versatile powder coatings contain binding agents, pigments, fillers and cross-linkers as well as optionally additives. By a binding agent is meant according to the invention the definition given in DIN 55 945. In other words, the binding agent comprises both the film former and non-volatile excipients such as plasticizers and driers. As a rule, the pulverulent powder coatings are deposited electrostatically before they are hardened by baking or by radiation energy.

Metallic effect pigments, inter alia, can be used to pigment the powder coatings. In powder coatings produced by means of mixing processes, however, it can prove to be problematic that damage to or destruction of the pigment platelets can occur due to the shearing forces acting on the pigment platelets during the extrusion and grinding process. In particular, the luster and thus also the visual effect of such pigmented applications can be negatively affected by this.

For this reason, for example in the dry-blend process the metallic effect pigments are admixed with the base powder coating only after the grinding. However, this has the disadvantage that a possible separation of pigment and powder coating occurs during the varnish application due to the different loading behavior of the individual varnish constituents. An irregular optical effect results from this in the form of the depletion or accumulation of pigment during the powder coating application. Furthermore, the separation of pigment and binding agent leads to a modified composition of the "overspray". Alternatively, the so-called bonding method is used in which the pigment is fixed to the particles of the base varnish under heating. However, the production of such bonding powder coatings is relatively expensive. The production of the currently most cost-favorable powder coatings takes place using mixing methods. Here the pigments are mixed together with all the other raw materials, extruded and ground.

Because substrates coated with powder coating are exposed to temperatures of 200° C. in a furnace after the powder coating application, this results in copper-containing metal pigments being oxidized, which manifests itself in an undesired color change. It has been shown that even a very thick plastic layer is unable to prevent the oxidation. However, such a plastic layer brings about a good chemicals stability. Furthermore, it has been shown that a metal oxide layer effectively prevents the oxidation. However, the chemicals stability of such a layer is not sufficient. The application of both layers in usual quantity ratios, however, leads to a serious deterioration of the optical properties. However, it has surprisingly been shown that the desired stabilities are achieved by the coating to be applied according to the invention, while the optical properties of the pigment are almost or completely retained.

Coil-Coating

Coil-coating is also known as a very environmentally friendly coating method. Here, coating and drying take place continuously in a closed system, wherein the rinsing of chemical residues can also be dispensed with in the no-rinse method. Furthermore, an application efficiency of almost 100% can be achieved by an optimized process control, while in other respects in most varnishing methods there are for example greater losses due to overspraying. However, because the varnish is baked at temperatures of from 240 to 280° C. in coil-coating, here too oxidation phenomena are observed in conventional copper-containing metal pigments analogously to powder coating. The above-discussed problems and observations in relation to the powder coating therefore also apply to coil-coating.

Nail Polish

Uncoated copper-containing pigments very readily release copper ions which lead to a green discoloration e.g. in nitrocellulose varnishes. In addition, the pigments settle at the bottom over time and can no longer be shaken up or redispersed after even a few days. Thus, the nail polish can no longer be used after a few days. A metal oxide layer can curtail the release of copper ions a little, but no satisfactory storage stabilities can be achieved. However, it was surprisingly observed that platelet-shaped copper-containing metal pigments which are coated according to the invention with at least one plastic layer and at least one metal oxide layer have storage stabilities over 6 months, without a noticeable deterioration of the optical qualities, compared with the uncoated pigment, occurring. Within the storage time, the platelet-shaped copper-containing pigments according to the invention which have settled at the bottom could always be shaken up or easily redispersed again. Moreover, no green discoloration appeared during the storage time.

Polymers

Copper-containing metal pigments incorporated into polymers, in particular platelet-shaped copper-containing metal pigments, are often oxidized during processing, whereby for example the color changes. This can also be prevented only conditionally by changes in the process conditions, whereby for example the reproduction of a desired hue becomes almost impossible. It was surprisingly found that the platelet-shaped copper-containing metal pigments according to the invention have a sufficient stability in order to make possible a processing under standard conditions, with the result that no noticeable or no change whatever in the hue of the platelet-shaped copper-containing metal pigments according to the invention is observed.

The polymers used preferably comprise here thermoplastic, thermosetting or elastomeric polymers. Thermoplastic polymers are particularly preferred here.

All thermoplastics known to a person skilled in the art come into consideration as thermoplastic polymers. Suitable thermoplastic polymers are described for example in the Kunststoff-Taschenbuch, ed. Saechtling, 25$^{th}$ edition, Hanser-Verlag, Munich, 1992, in particular chapter 4 as well as references cited therein, and in the Kunststoff-Handbuch, ed. G. Becker and D. Braun, Volumes 1 to 11, Hanser-Verlag, Munich, 1966 to 1996.

By way of example, the following may be named as suitable thermoplastics: polyoxyalkylenes, polycarbonates (PC), polyesters such as polybutylene terephthalate (PBT) or polyethylene terephthalate (PET), polyolefins such as polyethylene or polypropylene (PP), poly(meth)acrylates, polyamides, vinylaromatic (co)polymers such as polystyrene, impact-modified polystyrene such as HIPS, or ASA, ABS or AES polymers, polyarylene ethers such as polyphenylene ether (PPE), polysulfones, polyurethanes, polylactides, halogen-containing polymers, polymers containing imide groups, cellulose esters, silicone polymers or thermoplastic elastomers. Mixtures of different thermoplastics can also be used as materials for the polymer shaped parts. These mixtures can be single- or multi-phase polymer blends.

The polymers can consist of identical or different thermoplastics or thermoplastic blends.

Polyoxyalkylene homo- or copolymers, in particular (co)polyoxymethylenes (POM), and methods for the production thereof are known per se to a person skilled in the art and described in the literature. Suitable materials are commercially available under the brand name Ultraform® (BASF AG, Germany). Quite generally, these polymers have at least 50 mol.-% recurring units of —CH$_2$O— in the polymer main chain. The homopolymers are generally produced by polymerization of formaldehyde or trioxane, preferably in the presence of suitable catalysts. Polyoxymethylene copolymers and polyoxymethylene terpolymers are preferred. The preferred polyoxymethylene (co)polymers have melting points of at least 150° C. and molecular weights (weight-average value) M in the range of from 5,000 to 200,000, preferably from 7,000 to 150,000 g/mol. End-group-stabilized polyoxymethylene polymers which have C—C bonds at the chain ends are particularly preferred.

Suitable polycarbonates are known per se and can be obtained e.g. according to DE-B-1 300 266 by interfacial polycondensation or according to DE-A-14 95 730 by reacting biphenyl carbonate with bisphenols. Preferred bisphenol is 2,2-di(4-hydroxyphenyl)propane, generally called bisphenol A. The relative viscosity of these polycarbonates generally lies in the range of from 1.1 to 1.5, in particular 1.28 to 1.4 (measured at 25° C. in a 0.5 wt.-% solution in dichloromethane). Suitable polycarbonates are commercially available under the brand name Lexan® (GE Plastics B. V., Holland).

Suitable polyesters are also known per se and described in the literature. They contain an aromatic ring in the main chain which originates from an aromatic dicarboxylic acid. The aromatic ring can also be substituted, e.g. by halogen such as chlorine and bromine or by $C_1$-$C_4$ alkyl groups such as methyl, ethyl, i- or n-propyl and n-, i- or tert-butyl groups. The polyesters can be produced by reacting aromatic dicarboxylic acids, esters thereof or other ester-forming derivatives of same with aliphatic dihydroxy compounds in a manner known per se. Naphthaline dicarboxylic acid, terephthalic acid and isophthalic acid or mixtures thereof are to be named as preferred dicarboxylic acids. Up to 10 mol.-% of the aromatic dicarboxylic acids can be replaced by aliphatic or cycloaliphatic dicarboxylic acids such as adipic acid, azelaic acid, sebacic acid, dodecane diacids and cyclohexane dicarboxylic acids. Of the aliphatic dihydroxy compounds, dials with 2 to 6 carbon atoms, in particular 1,2-ethanediol, 1,4-butanediol, 1,6-hexanediol, 1,4-hexanedial, 1,4-cyclohexanediol and neopentyl glycol or mixtures thereof are preferred. Polyalkylene terephthalates which derive from alkanediols with 2 to 6 C atoms are to be named as particularly preferred polyesters. Of these, polyethylene terephthalate (PET), polyethylene naphthalate and polybutylene terephthalate (PBT) are preferred in particular. These products are commercially available e.g. under the trade names Rynite® (PET; from DuPont, USA) or Ultradur® (PBT; BASF AG). The viscosity number of the polyesters generally lies in the range of from 60 to 200 ml/g (measured in a 0.5 wt.-% solution in a phenol/o-dichlorobenzene mixture (wt. ratio 1:1 at 25° C.)).

Suitable polyolefins are quite generally represented by polyethylene and polypropylene as well as copolymers based on ethylene or propylene, optionally also with higher α-olefins. Corresponding products can be obtained e.g. under the trade names Lupolen® or Novolen®. By polyolefins are also meant ethylene-propylene elastomers and ethylene-propylene terpolymers.

Among the poly(meth)acrylates, in particular polymethyl methacrylate (PMMA) as well as copolymers based on methyl methacrylate with up to 40 wt.-% further copolymerizable monomers, such as n-butyl acrylate, t-butyl acrylate or 2-ethylhexyl acrylate are to be named, such as can be obtained for example under the names Lucryl® (BASF AG) or Plexiglas® (Röhm GmbH, Germany). Within the meaning of the invention, these also include impact-modified poly(meth)acrylates as well as mixtures of poly(meth)acrylates and SAN polymers which are impact-modified with polyacrylate rubbers (e.g. the commercial product Terlux® from BASF AG).

Suitable polyamides are those with aliphatic partially crystalline or partially aromatic or amorphous structure of any type and blends thereof, including polyetheramides such as polyether block amides. By polyamides are meant all known polyamides. Suitable polyamides generally have a viscosity number of from 90 to 350, preferably 110 to 240 ml/g (determined in a 0.5 wt.-% solution in 96 wt.-% sulfuric acid at 25° C. according to ISO 307). Semi-crystalline or amorphous resins with a molecular weight (weight-average value) of at least 5,000 g/mol, such as described e.g. in U.S. Pat. Nos. 2,071,250, 2,071,251, 2,130,523, 2,130,948, 2,241,322, 2,312,966, 2,512,606 and 3,393,210, are preferred.

Examples of this are polyamides which derive from lactams with 7 to 13 ring members, such as polycaprolactam, polycapryllactam and polylauryllactam, as well as polyamides which are obtained by reacting dicarboxylic acids with diamines.

Alkanedicarboxylic acids with 6 to 12, in particular 6 to 10 carbon atoms and aromatic dicarboxylic acids can be used as dicarboxylic acids. Here, adipic acid, azelaic acid, sebacic acid, dodecane diacid (=decanedicarboxylic acid) and/or isophthalic acid may be named as acids.

Alkanediamines with 6 to 12, in particular 6 to 8 carbon atoms, as well as m-xylylenediamine, di-(4-aminophenyl)methane, di-(4-aminocyclohexyl)methane, 2,2-di-(4-aminophenyl)propane or 2,2-di-(4-aminocyclohexyl)propane are particularly suitable as diamines.

Preferred polyamides are polyhexamethylene adipic acid amide (PA 66), e.g. the commercial product Ultramid® A (BASF AG), and polyhexamethylene sebacic acid amide (PA 610), e.g. the commercial product Nylon® 610 (from DuPont), polycaprolactam (PA 6), e.g. the commercial product Ultramid® B (BASF AG) as well as copolyamide 6/66, in particular with a proportion of from 5 to 95 wt.-% caprolactam units, e.g. the commercial product Ultramid® C (BASF AG). PA 6, PA 66 and copolyamide 6/66 are particularly preferred.

Moreover, polyamides can also be used which can be obtained e.g. by condensation of 1,4-diaminobutane with adipic acid at increased temperature (polyamide-4,6). Production methods for polyamides of this structure are described e.g. in EP-A 38 094, EPA 38 582 and EP-A 39 524.

Further examples are polyamides which can be obtained by copolymerization of two or more of the above-named monomers, or mixtures of several polyamides, wherein the mixing ratio is as desired.

Furthermore, such partially aromatic copolyamides such as PA 6/6T and PA 66/6T the triamine content of which is less than 0.5, preferably less than 0.3 wt.-% (see EP-A 299 444), have proved to be particularly advantageous. The production of the partially aromatic copolyamides with low triamine content can take place according to the methods described in EP-A 129 195 and 129 196.

Further suitable thermoplastic materials are represented by vinylaromatic (co)polymers. The molecular weight of these commercially available polymers known per se generally lies in the range of from 1,500 to 2,000,000, preferably in the range of from 70,000 to 1,000,000 g/mol.

By way of example, vinylaromatic (co)polymers of styrene, chlorostyrene, α-methylstyrene and p-methylstyrene are named; comonomers such as (meth)acrylonitrile or (meth)acrylic acid ester can also be part of the structure in inferior proportions, preferably not more than 20 wt.-%, in particular not more than 8 wt.-%. Particularly preferred vinylaromatic (co)polymers are polystyrene, styrene-acrylonitrile copolymers (SAN) and impact-modified polystyrene (HIPS=High Impact Polystyrene). It is understood that mixtures of these polymers can also be used. The production preferably takes place according to the method described in EP-A-302 485.

Furthermore, ASA, ABS and AES polymers (ASA=acrylonitrile-styrene-acrylester, ABS=acrylonitrile-butadiene-styrene, AES=acrylonitrile-EPDM rubber-styrene) are particularly preferred. These impact-resistant vinylaromatic polymers contain at least one rubber elastic graft polymer and a thermoplastic polymer (matrix polymer). Generally, a styrene/acrylonitrile polymer (SAN) is used as matrix material. Graft polymers are preferably used which contain, as rubber, a diene rubber based on dienes, such as e.g. butadiene or isoprene, (ABS);

an alkyl acrylate rubber based on alkyl esters of acrylic acid, such as n-butyl acrylate and 2-ethylhexyl acrylate, (ASA);

an EPDM rubber based on ethylene, propylene and a diene, (AES); or mixtures of these rubbers or rubber monomers.

The production of suitable ABS polymers is found e.g. described in detail in the German patent application DE-A 19728629. For the production of ASA polymers, EP-A 99 532 can e.g. be consulted. Details on the production of AES polymers are disclosed for example in U.S. Pat. No. 3,055,859 or in U.S. Pat. No. 4,224,419. Reference is hereby made expressly to the patent specifications named in this paragraph.

By polyarylene ethers are preferably meant both polyarylene ethers per se and polyarylene ether sulfides, polyarylene ether sulfones or polyarylene ether ketones. The arylene groups thereof can be the same or different and independently of each other mean an aromatic radical with 6 to 18 C atoms. Examples of suitable arylene radicals are phenylene, bisphenylene, terphenylene, 1,5-naphthylene, 1,6-naphthylene, 1,5-anthrylene, 9,10-anthrylene or 2,6-anthrylene. Of these, 1,4-phenylene and 4,4'-biphenylene are preferred. These aromatic radicals are preferably not substituted. However, they can carry one or more substituents. Suitable polyphenylene ethers are commercially available under the name Noryl® (GE Plastics B. V., Holland).

In general, the polyarylene ethers have average molecular weights M (numerical average) in the range of from 10,000 to 60,000 g/mol and viscosity numbers of from 30 to 150 ml/g. The viscosity numbers are measured depending on the solubility of the polyarylene ethers either in 1 wt.-% N-methylpyrrolidone solution, in mixtures of phenol and o-dichlorobenzene or in 96% sulfuric acid at in each case 20° C. and 25° C.

The polyarylene ethers are known per se or can be produced according to methods known per se.

Preferred process conditions for the synthesis of polyarylene ether sulfones or ketones are described for example in EP-A 113 112 and EP-A 135 130. As a rule, polyarylene ether sulfones have a melting point of at least 320° C., polyarylene ether ketones have a melting point of at least 370° C. Suitable polyphenylene ether sulfones are commercially available e.g. under the name Ultrason® E (BASF AG), suitable polyphenylene ether ketones under the name Victrex®.

In addition, polyurethanes, polyisocyanurates and polyureas are suitable for coloring with platelet-shaped copper-containing metal pigments according to the invention. Soft, semi-hard or hard thermoplastic or cross-linked polyisocyanate polyaddition products, for example polyurethanes, polyisocyanurates and/or polyureas, in particular polyurethanes, are generally known and commercially available i.a. under the name Elastolan® (Elastogran GmbH, Germany). Their production is widely described and usually takes place by reacting isocyanates with compounds reactive vis-á-vis isocyanates under generally known conditions. The reaction is preferably carried out in the presence of catalysts and/or excipients. If foamed polyisocyanate polyaddition products are involved, these are produced in the presence of usual foaming agents.

The aromatic, arylaliphatic, aliphatic and/or cycloaliphatic organic isocyanates known per se, preferably diisocyanates, come into consideration as isocyanates.

For example, generally known compounds with a molecular weight of from 60 to 10,000 g/mol and a functionality vis-á-vis isocyanates of from 1 to 8, preferably 2 to 6, can be used as compounds reactive vis-á-vis isocyanates (in the case of thermoplastic polyurethanes TPU functionality approx. 2), for example polyols with a molecular weight of from 500 to 10,000 g/mol, e.g. polyether polyols, polyester polyols, polyetherpolyester polyols, and/or diols, triols and/or polyols with molecular weights smaller than 500 g/mol.

Polylactides, thus polymers of lactic acid, are known per se or can be produced according to methods known per se and can also be used in conjunction with the platelet-shaped copper-containing metal pigments according to the invention. In addition to polylactide, co- or block copolymers based on lactic acid and further monomers can also be used. Linear polylactides are usually used. However, branched lactic acid polymers can also be used. For example, multifunctional acids or alcohols can serve as branching agents.

In particular, polymers of vinyl chloride are to be named as suitable halogen-containing polymers, in particular polyvinyl chloride (PVC) such as hard PVC and soft PVC, and copolymers of vinyl chloride such as PVC-U molding compounds.

Furthermore, fluorine-containing polymers come into consideration, in particular polytetrafluoroethylene (PTFE), tetrafluoroethylene-perfluoropropylene copolymers (FEP), copolymers of tetrafluoroethylene with perfluoroalkylvinylether, ethylene-tetrafluoroethylene copolymers (ETFE); polyvinylidene fluoride (PVDF), polyvinyl fluoride (PVF), polychlorotrifluoroethylene (PCTFE), and ethylene-chlorotrifluoroethylene copolymers (ECTFE).

Polymers containing imide groups are in particular polyimides, polyetherimides, and polyamide-imides.

Suitable cellulose esters are for instance cellulose acetate, cellulose acetobutyrate, and cellulose propionate.

In addition, silicone polymers also come into consideration as thermoplastics. Silicone rubbers are suitable in particular. These are usually polyorganosiloxanes which have groups capable of cross-linking reactions.

Such polymers are described for example in Römpp Chemie Lexikon, CD-ROM version 1.0, Thieme Verlag Stuttgart 1995.

The platelet-shaped copper-containing metal pigments according to the invention can also be introduced into thermoplastic elastomers (TPE). TPEs can be processed like thermoplastics, but have rubber-elastic properties. TPE block polymers, TPE graft polymers and segmented TPE copolymers of two or more monomer building blocks are suitable. Particularly suitable TPEs are thermoplastic polyurethane elastomers (TPE-U or TPU), styrene oligoblock copolymers (TPE-S) such as SBS (styrene-butadiene-styrene-oxy block copolymer) and SEES (styrene-ethylene-butylene-styrene block copolymers, available by hydrogenation of SBS), thermoplastic polyolefin elastomers (TPE-O), thermoplastic polyester elastomers (TPE-E), thermoplastic polyamide elastomers (TPE-A) and in particular thermoplastic vulcanisates (TPE-V). A person skilled in the art will find details on TPEs in G. Holden et al., Thermoplastic Elastomers, $2^{nd}$ edition, Hanser Verlag, Munich 1996.

In addition to the platelet-shaped copper-containing metallic effect pigments according to the invention, usual additives can furthermore be contained in the polymers. These additives can be selected for example from the group which consists of fillers, additives, plasticizers, lubricants or mold release agents, impact modifiers, pigments, dyes, flame retardants, static inhibitors, optical brighteners, antioxidants, antimicrobial biostabilizers, chemical foaming agents or organic cross-linking agents as well as other additives and mixtures thereof.

It was found that, below 0.1 wt.-% of the platelet-shaped copper-containing metal pigments according to the invention, relative to the total weight of the polymer containing metal pigment, the coloring effect is much less pronounced. Furthermore, it was found that, above 10 wt.-%, relative to the total weight of the polymer containing metal pigment, the mechanical strength decreases. According to particular preferred embodiments, the proportion of the platelet-shaped copper-containing metal pigments according to the invention in the polymer is 0.01 to 10 wt.-%, preferably 0.1 to 8 wt.-%, in each case relative to the total weight of the polymer containing metal pigment. In addition, it is preferred that the proportion of the platelet-shaped copper-containing metal pigments according to the invention in the polymer is 0.25 to 5 wt.-%, still further preferably 0.5 to 2.5 wt.-%, in each case relative to the total weight of the polymer containing metal pigment.

The plastics containing the platelet-shaped copper-containing metal pigment according to the invention can also be used in laser marking. During irradiation, the laser beam heats the platelet-shaped copper-containing metal pigments according to the invention struck by it, which then lead to a visible change in the plastic surrounding the metal pigments.

It has been established that the possibility of laser marking greatly diminishes below 0.0005 wt.-%, relative to the total weight of the polymer containing the platelet-shaped copper-containing metal pigment according to the invention. On the other hand, the optical properties of the polymer are already greatly influenced at a concentration of more than 0.7 wt.-%, relative to the total weight of the polymer containing the platelet-shaped copper-containing metal pigment according to the invention. According to particular preferred embodiments, the proportion of the platelet-shaped copper-containing metal pigments in the polymer is therefore 0.0005 to 0.7 wt.-%, preferably 0.001 to 0.5 wt.-%, in each case relative to the total weight of the polymer containing metal pigment. In addition, it is preferred in particular embodiments that the proportion of the platelet-shaped copper-containing metal pigments according to the invention is 0.005 to 0.5 wt.-%, still further preferably 0.01 to 0.1 wt.-%, in each case relative to the total weight of the polymer containing metal pigment.

Methods:

The object of the invention is furthermore achieved by providing a method for producing a copper-containing pigment according to the invention, wherein the method comprises the following steps:

(1a) coating platelet-shaped copper-containing metal pigments with metal oxide, (1b) coating the platelet-shaped copper-containing metal pigments coated with metal oxide obtained in step (1a) with the educt(s) of the chemically non-reactive plastic layer, (1c) curing or polymerizing the copper-containing metal pigments coated with the educt(s) of the chemically non-reactive plastic layer in step (1b) or (2a) coating platelet-shaped copper-containing metal pigments with the educt(s) of the chemically non-reactive plastic layer, (2b) curing or polymerizing the platelet-shaped copper-containing metal pigments coated with the educt(s) of the chemically non-reactive plastic layer in step (2a), (2c) coating the platelet-shaped copper-containing metal pigments coated with chemically non-reactive plastic layer obtained in step (2b) with metal oxide.

The platelet-shaped copper-containing metal pigments obtained in step (1c) or step (2b) then have a chemically non-reactive plastic layer.

In particular preferred embodiments, the above-named coatings with metal oxide and/or the chemically non-reactive plastic layer are carried out repeatedly or with other metal oxides or educts of a chemically non-reactive plastic layer, in order to provide a coating with several metal oxide layers and/or chemically non-reactive plastic layers.

The coating of the platelet-shaped copper-containing metal pigments with metal oxide can be carried out in a conventional manner. For example, the metal oxides can be applied accompanied by hydrolysis of corresponding metal salts, such as for example metal halides, in particular metal chlorides.

The metal oxide layers are preferably applied by means of sol-gel methods. Here, the corresponding metal alkoxides are hydrolyzed accompanied by the addition of water, as well as preferably acids or bases as catalysts, wherein the corresponding metal oxides and/or metal oxide hydrates are deposited on the copper-containing metal pigments and cover them.

The alkoxy groups are preferably methoxy, ethoxy, propoxy, butoxy and/or pentoxy groups. The alkoxy groups are extremely preferably methoxy and/or ethoxy groups.

The coating with metal oxide by means of sol-gel methods usually takes place in organic solvent in the presence of small quantities of water, such as for example 1 to 10 vol.-%, preferably 2 to 5 vol.-%, water, relative to the total volume of the water-containing organic solvent.

Alcohols, glycols, esters, ketones as well as mixtures of these solvents are preferably used as organic solvents. The use of alcohols, glycols or mixtures thereof is particularly suitable. Alcohols are particularly preferably used.

The alcohol is preferably selected from the group which consists of methanol, ethanol, isopropanol, n-propanol, t-butanol, n-butanol, isobutyl alcohol, pentanol, hexanol and mixtures thereof. Ethanol and/or isopropanol have proved to be very suitable.

Butyl glycol, propyl glycol, ethylene glycol or mixtures thereof are preferably used as glycol.

The platelet-shaped copper-containing metal pigments are dispersed in the organic solvent accompanied by the optional addition of water. Either acid or base is added, as catalyst, to this suspension.

The dispersion is preferably heated. The water necessary for hydrolysis can be already contained in the organic solvent or added at a later point in time.

The acid can be organic and/or inorganic acid. The organic acid is preferably selected from the group which consists of formic acid, acetic acid, propanoic acid, oxalic acid, malonic acid, maleic acid, succinic acid, anhydrides of the named acids and mixtures thereof. Formic acid, acetic acid, oxalic acid or mixtures thereof are preferably used.

The inorganic acid can be selected be selected from the group which consists of nitric acid, sulfuric acid, phosphoric acid, hydrochloric acid, boric acid, hydrofluoric acid and mixtures thereof. Nitric acid and/or hydrofluoric acid are preferably used.

According to a preferred variant, the basic catalyst is an amine. This can be primary, secondary or tertiary amines.

According to a preferred embodiment, the amine is selected from the group which consists of dimethylethanolamine (DMSA), monoethanolamine (MEA), diethanolamine (DEA), triethanolamine (TEA), ethylenediamine (EDA), t-butylamine, monomethylamine, dimethylamine, trimethylamine, monoethylamine, diethylamine, triethylamine, diisopropylethylamine, pyridine, pyridine derivatives, aniline, aniline derivatives, choline, choline derivatives, urea, urea derivative, hydrazine derivatives and mixtures thereof.

Ethylenediamine, monoethylamine, diethylamine, monomethylamine, dimethylamine, triethylamine or mixtures thereof have proved to be very suitable as basic aminic catalyst.

Of course, inorganic bases, such as ammonia, hydrazine, sodium hydroxide, potassium hydroxide, ammonium hydroxide, ammonium carbonate, ammonium hydrogen carbonate, sodium carbonate, sodium hydrogen carbonate, potassium carbonate, sodium hydrogen carbonate or mixtures thereof can also be used. Ammonia and/or hydrazine have proved to be very suitable.

According to an extremely preferred embodiment, tetraalkoxysilane is used as metal alkoxide. Tetramethoxysilane, tetraethoxysilane, tetraisopropoxysilane or condensates thereof or mixtures thereof are preferably used as tetraalkoxysilane. Tetraethoxysilane and/or oligomers of tetraethoxysilane have proved to be very suitable.

After application of the metal oxide layer, the platelet-shaped copper-containing metal pigments coated with metal oxide are preferably separated and the chemically non-reactive plastic layer is applied. The chemically non-reactive plastic layer can be constructed by polymerization of suitable monomers. The monomers can have functionalities which are selected from the group which consists of amino, hydroxy, thiol, epoxy, acrylate, methacrylate, vinyl, allyl, alkenyl, alkynyl, carboxy, carboxyl anhydride, isocyanate, cyanate, ureido, carbamate, ester groups and mixtures thereof.

In particular cross-linking, i.e. multifunctional (meth)acrylates, as monomers or reactive oligomers or polymers, are suitable as educts of the plastic layer. Examples of such compounds are:

allyl methacrylate, bisphenol A dimethacrylate, 1,3-butanediol dimethacrylate, 1,4-butanediol dimethacrylate, ethylene glycol dimethacrylate, 1,6-hexanediol diacrylate, 1,6-hexanediol dimethacrylate, diethylene glycol dimethacrylate, diurethane dimethacrylate, dipropylene glycol diacrylate, 1,12-dodecanediol dimethacrylate, ethylene glycol dimethacrylate, methacrylic acid anhydride, N,N-methylene-bis-methacrylamide, neopentyl glycol dimethacrylate, polyethylene glycol dimethacrylate, polyethylene glycol 200 diacrylate, polyethylene glycol 400 diacrylate, polyethylene glycol 400 dimethacrylate, tetraethylene glycol diacrylate, tetraethylene glycol dimethacrylate, tricyclodecane dimethanol diacrylate, tripropylene glycol diacrylate, triethylene glycol dimethacrylate, pentaerythritol triacrylate, trimethyloipropane triacrylate, trimethylolpropane trimethacrylate, tris-(2-hydroxyethyl)isocyanurate triacrylate, pentaerythritol tetraacrylate, dipentaerythritol pentaacrylate or mixtures thereof.

In particular embodiments, tri- and higher functional (meth)acrylates, in particular trifunctional (meth)acrylates, are preferred. The term "(meth)acrylate" within the meaning of the present invention comprises methacrylates and acrylates.

The curing or polymerization of vinyl- and/or (meth)acrylate-functional monomers during the production of the chemically non-reactive plastic layer can take place thermally in preferred embodiments.

In further preferred embodiments, the curing or polymerization takes place by radical polymerization using polymerization initiators, preferably radical initiators. These are peroxides or diazonium compounds that are customary in the trade and as a rule organic or inorganic. Examples of such compounds are:

acetylcyclohexane sulfonyl peroxide, bis(2,4-dichlorobenzoyl)peroxide, diisononanyl peroxide, dioctanoyl peroxide, diacetyl and dibenzoyl peroxide; peroxydicarbonates (e.g. diisopropyl peroxydicarbonate, di-n-butyl peroxydicarbonate, di-2-ethylhexyl peroxydicarbonate, dicyclohexyl peroxydicarbonate), alkyl perester (e.g. cumyl perneodecanoate, t-butyl perneodecanoate, t-amyl perpivalate, t-butyl per-2-ethylhexanoate, t-butyl perisobutyrate, t-butyl perbenzoate), dialkyl peroxides (e.g. dicumyl peroxide, t-butyl-cumyl peroxide, 2,5-dimethylhexane-2,5-di-t-butyl peroxide, di(t-butylperoxy isopropyl)benzene, di-t-butyl peroxide, or 2,5-dimethyl hexine-3-2,5-di-t-butyl peroxide), perketals (e.g. 1,1-bis-(t-butylperoxy)-3,3,5-trimethylcyclohexanone peroxide, methyl isobutyl ketone peroxide, methyl ethyl ketone peroxide, acetyl acetone peroxide), alkyl hydroperoxides (e.g. pinane hydroperoxide, cumolhydroperoxide, 2,5-dimethylhexane-2,5-dihydroperoxide or t-butyl hydroperoxide), azo compounds (e.g. 4-4'-azobis(4-cyanovaleric acid), 1,1'-azobis(cyclohexanecarboxylic acid nitrile), 1,1'-azobis(isobutyro acid amidine)dihydrochloride, 2,2'-azobis(isobutyronitrile), dimethyl 2,2'-azobis(2-methylpropionate) or persulfates such as sodium peroxodisulfate and potassium peroxodisulfate. 2,2'-azobis(isobutyronitrile) and dimethyl 2,2'-azobis(2-methylpropionate) are preferred. These compounds are commercially available from Aldrich Chemie, D-89552, Steinheim or Wako Chemicals GmbH, Fuggerstraβe 12, 41468 Neuss.

The educts of the plastic layer, for example reactive oligomers and/or polymers, can also reactive polymers which are selected from the group which consists of polyacrylates, poly(meth)acrylates, polyethers, polyesters, polyamines, polyamides, polyols, polyurethanes, polyolefins and mixtures thereof.

According to a variant of the invention, the platelet-shaped copper-containing metal pigments coated with metal oxide are dispersed in a, preferably organic, solvent and the suspension is brought to reaction temperature. The educts of the plastic layer are then added, for example in the form of organic monomers and/or reactive oligomers/polymers, as well as optionally polymerization initiators, for example by dropwise addition, whereby the chemically non-reactive plastic layer (organic polymer layer) is formed on the copper-containing pigments coated with metal oxide. The dispersion is preferably stirred or moved during the application of the plastic layer.

Of course, the chemically non-reactive plastic layer can also be applied by spraying the educts of the plastic layer, for example the organic monomers and/or reactive organic oligomers and/or reactive organic polymers, as well as optionally polymerization initiators, in a fluidized bed in which the copper-containing metal pigments coated with metal oxide are swirled.

According to a preferred variant of the invention, the coating takes place in a liquid phase.

According to a further variant of the invention, the application of the chemically non-reactive plastic layer takes place in the same solvent in which the metal oxide layer was applied. This method variant is a one-step method, unlike the above-described two-step method variant.

After application of the chemically non-reactive plastic layer, these are preferably filtered off from the suspension.

According to a further variant of the invention, the application of the chemically non-reactive plastic layer to the metal oxide layer takes place in the form of a thermal polymerization. It has been observed that in the case of this thermal polymerization, which is carried out without the addition of an initiator, smooth surfaces result.

According to a further variant of the invention, the application of the layers takes place in reverse order, i.e. the chemically non-reactive plastic layer is applied first and then the metal oxide layer.

The platelet-shaped copper-containing metal pigments according to the invention are preferably pelletized, granulated, extrusion-granulated, extruded, briquetted, tableted and are therefore present in a substantially low-dust, preferably dust-free, compacted form. The copper-containing metal pigments according to the invention can be easily handled in these dosage forms and are easily incorporated into coating agents, such as for example varnishes, paints, printer inks, powder coatings, plastics, cosmetics, etc.

According to a preferred variant, the platelet-shaped copper-containing metal pigments according to the invention are incorporated into powder coating.

According to a preferred variant of the invention, the chemically non-reactive plastic layer of the platelet-shaped copper-containing metal pigments is compatible with the binding agent or binding agent system of the powder coating.

The invention is described in more detail below with reference to examples, without being limited thereto.

EXAMPLES

Example 1

Example 1a: Metal Oxide Layer 250 g rich pale gold G900 (Eckart GmbH, Hartenstein, Germany) was dispersed in 500 g ethanol. After heating to 50° C., 26 g tetraethoxysilane (TEOS) was added. 80 ml of a 3% ammonia solution was then added over 3 h. Stirring followed for a further hour, the reaction mixture was filtered off and the product obtained as a paste.

Example 1b: Plastic Layer (Initiator Variant)

139 g of the paste obtained in Example 1a (rich pale gold G 900 encapsulated with metal oxide) (corresponds to 100 g metal pigment) was dispersed in 486 g ethanol, with the result that a 16 wt.-% dispersion formed. 1 g methacryloxypropyltrimethoxysilane (MEMO) was then added and the mixture was stirred for 30 min at 25° C. and for 1 h at 75° C. 250 ml of a solution of 1.5 g dimethyl 2,2'-azobis(2-methylpropionate) (trade name V 601; available from WAKO Chemicals GmbH, Fuggerstraβe 12, 41468 Neuss), 4.75 g methacryloxypropyltrimethoxysilane (MEMO) and 17.5 g trimethylolpropane trimethacrylate (TMPTMA) in white spirit was then added to the reaction mixture over 1 h. Stirring followed for a further 15 h at 75° C., the reaction mixture was filtered off and isolated as paste.

Example 1c: Plastic Layer (Thermal Variant)

139 g of the paste obtained in Example 1a (rich pale gold G900 encapsulated with metal oxide) (corresponds to 100 g metal pigment) was dispersed in 486 g white spirit D100, with the result that a 16 wt.-% dispersion formed. 1 g methacryloxypropyltrimethoxysilane (MEMO) was then added and the mixture was stirred for 15 min at 25° C. and for 3 h at 50° C. 240 ml of a solution of 5.8 g methacryloxypropyltrimethoxysilane (MEMO) and 17.5 g trimethylolpropane trimethacrylate (TMPTMA) in white spirit 0100 was then added at 130° C. over 2 h. After 15 h of stirring at 130° C., the reaction mixture was filtered off, washed with 800 ml white spirit D100 and isolated as paste.

Example 2

100 g pale gold Dorolan L 900 (Eckart GmbH, Hartenstein, Germany) was dispersed in 525 g white spirit D100, with the result that a 16 wt.-% dispersion formed. 1 g methacryloxypropyltrimethoxysilane (MEMO) was then added and the mixture was stirred for 1 h at 25° C. and for 3 h at 50° C. 240 ml of a solution of 4.6 g methacryloxypropyltrimethoxysilane (MEMO) and 13.75 g trimethylolpropane trimethacrylate (TMPTMA) in white spirit D100 was then added over 2 h at 130° C. Stirring followed for a further 15 h at 130° C., the reaction mixture was filtered off and isolated as paste.

Example 3

100 g fire red Dorolan L900 (Eckart GmbH, Hartenstein, Germany) was dispersed in 525 g white spirit D100, with the result that a 16 wt.-% dispersion formed. 1 g methacryloxypropyltrimethoxysilane (MEMO) was then added and the mixture was stirred for 1 h at 25° C. and for 3 h at 50° C. 240 ml of a solution of 19.35 g trimethylolpropane trimethacrylate (TMPTMA) in white spirit D100 was then added over 2 h at 130° C. Stirring followed for a further 15 h at 130° C., the reaction mixture was filtered off and isolated as paste.

Example 4

Analogously to Example 3, the same coating was carried out with copper Dorolan L900.

Example 5

100 g copper Dorolan L900 (Eckart GmbH, Hartenstein, Germany) was dispersed in 525 g white spirit D100, with the result that a 16 wt.-% dispersion formed. 1 g methacryloxypropyltrimethoxysilane (MEMO) was then added and the mixture was stirred for 1 h at 25° C. and for 3 h at 50° C. 240 ml of a solution of 18.35 g trimethylolpropane trimethacrylate (TMPTMA) in white spirit D100 was then added over 3 h at 130° C. The end of the addition was followed by stirring for a further 15 h at 130° C., the reaction mixture was filtered off and isolated as paste.

Example 6

100 g fire red Dorolan L 900 (Eckart GmbH, Hartenstein, Germany) was dispersed in 525 g white spirit D100, with the result that a 16 wt.-% dispersion formed. 1 g methacryloxypropyltrimethoxysilane (MEMO) was then added and the mixture was stirred for 1 h at 25° C. and for 3 h at 50° C. 240 ml of a solution of 18.35 g trimethylolpropane trimethacrylate (TMPTMA) in white spirit D100 was then added over 3 h at 130° C. The end of the addition was followed by stirring for a further 15 h at 130° C., the reaction mixture was filtered off and isolated as paste.

Example 7

100 g fire red Dorolan L 900 (Eckart GmbH, Hartenstein, Germany) was dispersed in 525 g white spirit, with the result that a 16 wt.-% dispersion formed. 1 g methacryloxypropyltrimethoxysilane (MEMO) was then added and the mixture was stirred for 1 h at 25° C. and for 3 h at 50° C. 240 ml of a solution of 12.85 g trimethylolpropane trimethacrylate (TMPTMA) in white spirit D00 was then added over 3 h at 130° C. The end of the addition was followed by stirring for a further 15 h at 130° C., the reaction mixture was filtered off and isolated as paste.

Example 8

Example 8a: Plastic Layer 200 g rich pale gold RBIG G900 (Eckart GmbH, Hartenstein, Germany) was dispersed in 1050 g ethanol, with the result that a 16 wt.-% dispersion formed. 1.3 g methacryloxypropyltrimethoxysilane (MEMO) and 4 g trimethylolpropane trimethacrylate (TMPTMA) were then added and the mixture was stirred for 1 h at 25° C. and for 3 h at 50° C. 100 ml of a solution of 42 g trimethylolpropane trimethacrylate (TMPTMA) and 1 g dimethyl 2,2'-azobis(2-methylpropionate) (trade name V 601; available from WAKO Chemicals GmbH, Fuggerstrβe 12, 41468 Neuss) in ethanol was then added over 3 h at 75° C. Stirring followed for a further 15 h at 75° C., the reaction mixture was filtered off and isolated as paste.

Example 8b: Metal Oxide Layer 104 g of the paste obtained in Example 8 (corresponds to 70 g pigment) was dispersed in 316 g ethanol, with the result that a solids content of 16.7 wt.-% results. 23.3 g tetraethoxysilane (TEOS) was then added and the reaction mixture was heated to 75° C. 100 ml of a solution of 2 g ethylenediamine (EDA) and 20 g water in ethanol was then added over 3 h at 75° C. Stirring followed for 15 h at 75° C., the reaction mixture was filtered off and the product obtained as a paste.

Example 9

Example 9a: Plastic Layer 200 g rich pale gold G900 (Eckart GmbH, Hartenstein, Germany) was dispersed in 1050 g ethanol, with the result that a 16 wt.-% dispersion formed. 1.3 g methacryloxypropyltrimethoxysilane (MEMO) was then added and the mixture was stirred for 1 h at 25° C. and for 3 h at 75° C. 100 ml of a solution of 28 g trimethylolpropane trimethacrylate (TMPTMA) and 0.9 g dimethyl 2,2'-azobis(2-methylpropionate) (trade name V 601; available from WAKO Chemicals GmbH, Fuggerstraße 12, 41468 Neuss) in ethanol was then added over 3 h at 75° C. Stirring followed for 15 h at 75° C., the reaction mixture was filtered off and isolated as paste.

Example 9b: Metal Oxide Layer 103 g of the paste obtained in Example 9a (corresponds to 70 g pigment) was dispersed in 333 g ethanol, with the result that a solids content of 16 wt.-% resulted. 7.56 g tetraethoxysilane (TEOS) was then added at 75° C. 100 ml of a solution of 0.65 g ethylenediamine (FDA) and 21 g water in ethanol was then added at 75° C. Stirring followed for 15 h at 75° C., the reaction mixture was filtered off and the product obtained as a paste.

Example 10

Analogously to the conditions described under Example 8 and/or 9, different coated platelet-shaped copper-containing metal pigments were produced.

TABLE 1

Educt quantities of Examples 10-1 to 10-11

| | Procedure analogous to | MEMO | TMPTMA 1st addition | TMPTMA 2nd addition | TEOS |
|---|---|---|---|---|---|
| CE 10-1 | 8a, 9b | 1.3 g | 4.0 g | 8 g | 8.1 g |
| CE 10-2 | 8a, 9b | 1.3 g | 4.0 g | 8 g | 13.1 g |
| CE 10-3 | 8a, 9b | 1.3 g | 4.0 g | 8 g | 18.8 g |
| Example 10-4 | 8a, 9b | 1.3 g | 4.0 g | 24 g | 3.8 g |
| Example 10-5 | 9a, 9b | 1.3 g | 4.0 g | 24 g | 8.0 g |
| Example 10-6 | 8a, 9b | 1.3 g | 4.0 g | 42 g | 2.5 g |
| Example 10-7 | 8a, 9b | 1.3 g | 4.0 g | 42 g | 7.5 g |
| Example 10-8 | 8a, 9b | 1.3 g | 4.0 g | 42 g | 23.3 g |
| CE 10-9 | 8a | 1.3 g | 4.0 g | 87 g | — |
| CE 10-10 | 8a, 9b | 1.3 g | 4.0 g | 60 g | 2 g |
| CE 10-11 | 8a, 9b | 1.3 g | 4.0 g | 6 g | 9.3 g |

CE: comparison example

Example 11

Analogously to the conditions described under Examples 1a and 5, different coated platelet-shaped copper-containing metal pigments were produced. Rich pale gold G900 served as starting material.

TABLE 2

Educt quantities of Examples 11-1 to 11-12

| | Procedure analogous to | TEOS | MEMO | TMPTMA |
|---|---|---|---|---|
| Example 11-1 | 1a, 5 | 17.5 g | 1 g | 16.8 g |
| Example 11-2 | 1a, 5 | 21.8 g | 1 g | 16.8 g |
| Example 11-3 | 1a, 5 | 26.0 g | 1 g | 16.8 g |
| Example 11-4 | 1a, 5 | 32.8 g | 1 g | 16.8 g |
| Example 11-5 | 1a, 5 | 62.0 g | 1 g | 16.8 g |
| Example 11-6 | 1a, 5 | 32.8 g | 1 g | 29 g |
| Example 11-7 | 1a, 5 | 62.0 g | 1 g | 29 g |
| Example 11-8 | 1a, 5 | 77.5 g | 1 g | 29 g |
| CE 11-9 | 1a, 5 | 32.8 g | 1 g | 4 g |
| CE 11-10 | 1a, 5 | 62 g | 1 g | 11 g |
| CE 11-11 | 1a, 5 | 5 g | 1 g | 16.8 g |
| CE 11-12 | 1a, 5 | 5 g | 1 g | 29 g |

CE: comparison example

Example 12

Application Example Powder Coating and Chemicals Test

The obtained pastes were dried under vacuum with a light inert gas stream at 100° C. and then sieved at 71-μm mesh size. The respective metallic effect pigment was incorporated together with the powder coating AL 96 as well as with 0.2% Aeroxide Alu C (from Evonik) by means of a ThermoMix for 4 minutes on level 4. The pigmentation level was 5.0 wt.-%, as a verifiable application behavior can be achieved with higher pigmentation.

The powder coating was therefore weighed out to 95.0 wt.-%. The total quantity of powder coating in the mixer was 300 g plus 0.6 g Aeroxide Alu C.

ThermoMix is a food processor customary in the trade (from Vorwerk). The added Aeroxide Alu C is $Al_2O_3$ particles which assume the function of an anti-caking agent in this application case. The powder coatings were applied using an OptiSelect (from ITWGema) in a powder enclosure customary in the trade. To assess the application properties, spraying was carried out into the powder compartment for 20 seconds according to the parameters given in Table 1, then the coating of the substrate was carried out and then the adhesion to the electrodes and the adhesion to the baffle were comparatively assessed. This method allows the long-term behavior of the pigments to be assessed during practice-oriented varnishing.

Furthermore, the spray pattern was evaluated using the baked powder coating. Attention was paid above all to the course, thus the smoothness of the surface structure, as well as to black, microscopically small defects, so-called black spots. Areas on the powder coating surface which are brought about by an inhomogeneous distribution of the metallic effect pigments are called black spots. As these phenomena lie in the macroscopic range, the eye of an expert in varnish technology is needed for the assessment of the phenomenon. In particular very smooth structures with a very smooth course without black spot phenomena are preferred.

The application behavior, the presence of black spots and the structure or the course of the powder coatings were assessed visually.

Chemicals Test

The coated test sheet was brought into a horizontal position. 5 drops of 10% HCl were applied with exposure times of 180, 150, 120, 90, and 60 min. In addition, 5 drops of 1 M NaOH were applied with exposure times of 180, 120, 60, 30 and 15 min.

The drops were then removed with water and the formerly covered surfaces were compared visually with the uncovered surfaces. Here, a rating scale of 0-3 (for each individual point) was used (0=no attack, 3 maximum decomposition of pigments). The ascertained points were then totaled.

followed for 3 minutes at 500 rpm with a toothed ring stirrer. The viscosity was 100"±10 in a DIN4 cup.

This batch of varnish was drawn down on an alkane-aluminum DIN: A4 sheet (No. 11) using a spiral doctor blade. The sheet was immediately transferred into a furnace at 280° for 55 sec. Then the sheet was quenched in a water bath (RT). After 24 h at the earliest, the chemicals test was then carried out.

TABLE 3

Chemicals test, powder coating

| Sample | $SiO_2$ content in wt.-% | Plastic content in wt.-% | Wt. ratio of $SiO_2$ to plastic | Chemicals test |
|---|---|---|---|---|
| CE: rich pale gold G900 | — | — | — | 18 |
| CE: Example 1a | 3.1 | — | — | 18 |
| Example 1b | 3.1 | 17.6 | 1:5.7 | 0 |
| Example 1c | 3.1 | 22.3 | 1:7.2 | 0 |
| CE: pale gold Dorolan L900 | 3.8 | — | — | 11 pt. |
| Example 2, pale gold Dorolan L900 + plastic layer | 3.8 | 22.5 | 1:5.9 | 0 pt. |
| CE: copper Dorolan L 900 | 3.1 | — | — | 11 pt. |
| Example 5: copper Dorolan L 900 + plastic layer | 3.1 | 19.1 | 1:6.2 | 0 pt. |
| CE: fire red Dorolan L 900 | 3.7 | — | — | 20 pt. |
| Example 6: fire red Dorolan L 900 + plastic layer | 3.7 | 19 | 1:5.1 | 0 pt. |
| Example 7: fire red Dorolan L 900 + plastic layer | 3.7 | 13.6 | 1:3.7 | 0 pt. |
| CE: rich pale gold RBIG G900 | — | — | — | 18 |
| CE 8a: rich pale gold RBIG G900 + plastic layer | — | 23.6 | — | 3 |
| Example 8b: rich pale gold RBIG G900 + plastic layer + $SiO_2$ | 9.8 | 23.6 | 1:2.4 | 0 |
| CE: rich pale gold G900 | — | — | — | 18 |
| CE 9a: rich pale gold G900 + plastic layer | — | 14.7 | — | 8 |
| Example 9b: rich pale gold G900 + plastic layer + $SiO_2$ | 3.3 | 14.7 | 1:4.5 | 0 |
| CE 10-1 | 3.3 | 5.7 | 1:1.7 | 14 |
| CE 10-2 | 4.6 | 5.7 | 1:1.2 | 12 |
| CE 10-3 | 6.0 | 5.7 | 1:1.0 | 13 |
| Example 10-4 | 1.7* | 13 | 1:7.6 | 0 |
| Example 10-5 | 3.3 | 14.7 | 1:4.5 | 0 |
| Example 10-6 | 1.2* | 23.6 | 1:19.7 | 0 |
| Example 10-7 | 3.0 | 23.6 | 1:7.9 | 0 |
| Example 10-8 | 9.8 | 23.6 | 1:2.4 | 0 |
| CE 10-9 | — | 46 | — | 0 |
| CE 10-10 | 0.7* | 30.2 | 1:43 | 0 |
| CE 10-11 | 3.7 | 5 | 1:1.4 | 4 |
| Example 11-1 | 2.0 | 16.2 | 1:8.1 | 0 |
| Example 11-2 | 2.5 | 15.7 | 1:6.3 | 0 |
| Example 11-3 | 3.0 | 16.7 | 1:5.6 | 0 |
| Example 11-4 | 3.6 | 16.6 | 1:4.6 | 0 |
| Example 11-5 | 6.7 | 16.2 | 1:2.4 | 0 |
| Example 11-6 | 3.6 | 27.3 | 1:7.6 | 0 |
| Example 11-7 | 6.6 | 26.7 | 1:4.0 | 0 |
| Example 11-8 | 8.5 | 28.2 | 1:3.3 | 0 |
| CE 11-9 | 3.6 | 4.6 | 1:1.3 | 5 |
| CE 11-10 | 7.2 | 11 | 1:1.5 | 2 |
| CE 11-11 | 0.8 | 16.7 | 1:20.9 | 4 |

CE: comparison example
n.d. = not determined
*theor. $SiO_2$ content
wt.-%: in each case relative to the uncoated copper-containing metal pigment Example 13: Application Example, Coil Coating and Chemicals Test The pastes obtained in the above-named experiments were used directly in the coil coating method. 8.0 g aluminum paste and 8.0 g Solvesso 150 were thoroughly dispersed with a spatula until the mixture was speck-free. 84.0 g PE varnish 42-00001 was then added and the mixture stirred before being diluted with 5.0 g Solvesso 150. Stirring The coated test sheet was brought into a horizontal position. One drop each of hydrochloric acid (HCl) 5% and of caustic soda solution (NaOH) 5% was applied to the sheet. The drop size should be 20 to 25 mm in diameter. The drops were then covered with a watch glass and left to stand for 48 h. The drops were then removed with water and the formerly covered surfaces were compared visually with the uncovered surfaces. Here, a rating scale of 0-3 was used (0=no attack, 3 maximum decomposition of pigments).

TABLE 4

Chemicals test, coil coating

| | SiO$_2$ content in wt.-% | Plastic content in wt.-% | Weight ratio of SiO$_2$ to plastic | Chemicals test |
|---|---|---|---|---|
| CE: rich pale gold G900 | — | — | — | 25 |
| CE: 1a | 3.1 | — | — | n.d. |
| Example 1b | 3.1 | 17.6 | 1:5.7 | 22 |
| Example 1c | 3.1 | 22.3 | 1:7.2 | 3 |

CE: comparison example
wt.-%: in each case relative to the uncoated copper-containing metal pigment

Example 14: Application Example, Powder Coating and Oxidation Test

Powder coating sheets were prepared from different examples/comparison examples and cross-linked for 12 and optionally also for 60 min at 200° C. in a furnace. It was shown that only in the case of Examples 8b, 9b, 10-5, 10-7 and 10-8 no color change as a result of oxidation of the metallic effect pigments occurred.

TABLE 5

Oxidation test, powder coatings

| Sample | Plastic content in wt.-% | SiO$_2$ content in wt.-% | Wt. ratio of SiO$_2$ to plastic | Oxidation | Hue after 12 min | Hue after 60 min |
|---|---|---|---|---|---|---|
| Starting color of the metal pigments: rich pale gold | | | | | | |
| CE: rich pale gold RBIG G900 | — | — | — | yes | dark | n.d. |
| CE 8a: rich pale gold RBIG G900 + plastic layer | 23.6 | — | — | yes | orange gold | n.d. |
| Example 8b: rich pale gold RBIG G900 + plastic layer + SiO$_2$ | 23.6 | 9.8 | 1:2.4 | no | rich pale gold | n.d. |
| CE: rich pale gold G900 | — | — | — | yes | dark | n.d. |
| CE 9a: rich pale gold G900 + plastic layer | 14.7 | — | — | yes | orange gold | n.d. |
| Example 9b: rich pale gold G900 + plastic layer + SiO$_2$ | 14.7 | 3.3 | 1:4.5 | no | rich pale gold | n.d. |
| Starting color of the metal pigments: pale gold | | | | | | |
| CE: 8a | — | 23.6 | — | yes | orange gold | dark gold |
| Example: 10-5 | 14.7 | 3.3 | 1:4.5 | no | pale gold | n.d. |
| Example: 10-7 | 23.6 | 3.0 | 1:7.9 | no | pale gold | n.d. |
| Example: 10-8 | 23.6 | 9.8 | 1:2.4 | no | pale gold | pale gold |
| CE: 10-9 | 46.0 | — | — | yes | orange gold | dark gold |
| CE: 10-10 | 30.2 | 0.7* | 1:43 | yes | orange gold | dark gold |
| CE: 10-11 | 5 | 3.7 | 1:1.4 | yes | a little darker | n.d. |

CE: comparison example
n.d.: not determined
*theor. SiO$_2$ content
wt.-%: in each case relative to the uncoated copper-containing metal pigment Furthermore, experiments were carried out in which the state of the oxidation was determined quantitatively by means of colorimetry. Here, the powder coating was applied to sheets and cross-linked for 10 min at 200° C. in a furnace. The lightness value (L value) of the obtained sheets was determined by means of a Minolta Spectrophotometer CM-508i.

Furthermore, the color difference (ΔL) as a result of a treatment at 200° C. lasting 60 min longer was determined for different ones of the above-named powder coatings. The examples according to the invention here showed a lightness deviation of less than 3 units, while the comparison examples showed a lightness deviation of more than 8 units, and thus a strong oxidation.

TABLE 6

Oxidation test, powder coatings, determination by means of colorimetry

| Sample | Plastic content in wt.-% | SiO$_2$ content in wt.-% | Wt. ratio of SiO$_2$ to plastic | Oxidation | L value | ΔL |
|---|---|---|---|---|---|---|
| Example 11-1 | 2.0 | 16.2 | 1:8.1 | no | 62.7 | -2.4 |
| Example 11-2 | 2.5 | 15.7 | 1:6.3 | no | 62.6 | -2.6 |
| Example 11-3 | 3.0 | 16.7 | 1:5.6 | no | 63.7 | n.d. |
| Example 11-4 | 3.6 | 16.6 | 1:4.6 | no | 64.1 | -2.5 |
| Example 11-5 | 6.7 | 16.2 | 1:2.4 | no | 64.4 | n.d. |
| Example 11-6 | 3.6 | 27.3 | 1:7.6 | no | 63.3 | n.d. |
| Example 11-7 | 6.6 | 26.7 | 1:4.0 | no | 65.3 | n.d. |
| Example 11-8 | 8.5 | 28.2 | 1:3.3 | no | 64.2 | n.d. |
| CE 11-11 | 0.8 | 16.7 | 1:20.9 | yes | 61.4 | -8.1 |
| CE 11-12 | 0.7 | 27.9 | 1:39.9 | yes | 61.9 | -8.4 |

CE: comparison example
n.d.: not determined
wt.-%: in each case relative to the uncoated copper-containing metal pigment

Example 15: Application Example—Nail Polish

The metallic effect pigments were stirred with a pigmentation of 4 wt.-% into base 359 (from International Lacquers) with a brush and then transferred into nail polish bottles customary in the trade. The nail polish bottles were then stored a) at RT and b) in a furnace with a temperature of 40° C. for 6 months. During the storage time, it was visually evaluated whether a green discoloration set in. In addition, it was tested whether the pigments which have settled at the bottom could be shaken up or redispersed again. If either green discoloration occurred or if the pigment could no longer be shaken up or redispersed, the storage test was regarded as failed.

TABLE 7

Storage stability test, nail polish

| | Plastic content in wt.-% | SiO$_2$ content in wt.-% | Wt. ratio of SiO$_2$ to plastic | Storage stability at RT | Storage stability at 40° C. |
|---|---|---|---|---|---|
| CE: pale gold Dorolan L900 | — | 3.8 | — | 10 days | 3 days |
| Example 2: pale gold Dorolan L900 + plastic layer | 22.5 | 3.8 | 1:5.9 | >6 months | >6 months |
| CE: fire red Dorolan L900 | — | 3.7 | — | 7 days | 6 days |
| Example 3: fire red Dorolan L900 + plastic layer | 19.0 | 3.7 | 1:5.1 | >6 months | >6 months |
| CE: copper Dorolan L900 | — | 3.1 | — | 6 days | 6 days |
| Example 4: copper Dorolan L900 + plastic layer | 18.9 | 3.1 | 1:6.1 | >6 months | >6 months |

CE: comparison example
wt.-%: in each case relative to the uncoated copper-containing metal pigment It was shown that the SiO$_2$ coating alone is unable to guarantee a storage time of >6 months. Only by the additional plastic layer could a storage stability of >6 months be achieved.

Example 16: Application Example—Polymer

Different copper-containing metallic effect pigments were processed, mixed with thermoplastic polypropylene (PP) (R 771-10; from DOW, Germany, Wesseling), using the injection molding process to form disks (surface area 42×60 mm, thickness 2 mm).

To produce a 1 wt.-% mixture, the process was as follows:
495 g polypropylene granules (PP) and 4.95 g of the copper-containing pigment were mixed in a tumbling mixer and then processed in a twin-screw extruder (from Bersdorff, Germany, diameter 25 mm, 28UD) without the addition of further additives at a processing temperature of approx. 230° C. to form granules. These granules were then processed by means of an injection molding machine (Arburg Allrounder 221-55-250) at 260° C. to form the sample platelets with the above-named dimensions. The test for oxidation of the metal pigment took place by comparing the hue of the above-named platelets with reference platelets, the processing of which (production of granules and injection molding) was carried out at 190° C. For this, a Byk-mac from Byk-Gardner was used, wherein a ΔE<3 proved oxidation stability.

TABLE 8

Application example - Oxidation test, polymer

| Sample | Plastic content in wt.-% | SiO$_2$ content in wt.-% | Wt. ratio of SiO$_2$ to plastic | Oxidation |
|---|---|---|---|---|
| CE: rich pale gold G900 | — | — | — | yes |
| CE: Example 1a | — | 3.1 | — | yes |
| Example 1b | 17.6 | 3.1 | 1:5.7 | no |
| CE: rich pale gold RBIG G900 | — | — | — | yes |
| CE 8a: rich pale gold RBIG G900 + plastic layer | 23.6 | — | — | yes |
| Example 8b: rich pale gold RBIG G900 + plastic layer + SiO$_2$ | 23.6 | 9.8 | 1:2.4 | no |

CE: comparison example
wt.-%: in each case relative to the uncoated copper-containing metal pigment Example 17: Application Example—Water-in-Silicone Body Lotion

TABLE 9

Application example - Water-in-silicone body lotion

| INCI name | Product name | wt.-% | Manufacturer/supplier |
|---|---|---|---|
| Phase A | | | |
| Cyclopentasiloxane (and) Dimethiconol | Dow Corning 1501 | 11.20 | Dow Corning |
| Cyclopentasiloxane | Xiameter PMX-0245 Cyclosiloxane | 5.75 | Dow Corning |
| Cyclopentasiloxane (and) PEG/PPG-18/18 Dimethicone | Dow Corning 5225 C | 13.80 | Dow Corning |
| C 30-45 Alkyl Methicone | Dow Corning Cosmetic Wax AMS-C30 | 3.45 | Dow Corning |
| Copper-containing metal pigment according to Example 2 | | 1.00 | |
| Phase B | | | |
| Polysorbate 20 | Tween 20 | 0.60 | Croda |
| Phenoxyethanol (and) Methylparaben (and) Ethylparaben (and) Butylparaben (and) Probylparaben (and) Isobutylparaben | Uniphen P-23 | 0.35 | Induchem |
| Sodium Chloride | Sodium chloride | 0.75 | VWR |
| Aqua | Water | 63.10 | |

The copper-containing metallic effect pigment can be used in a range of from 0.2 to 2.5 relative to the total weight of the formulation. The balance can be made up with water.

Phase A was mixed and heated to 75° C., Phase B was heated to 70° C. after mixing, then Phase B was added slowly to Phase A accompanied by homogenization. Accompanied by stirring, the emulsion was cooled and poured into an appropriate container.

Example 18: Application Example—Eyeshadow Cream

TABLE 10

| \multicolumn{4}{c}{Application example - Eyeshadow cream} | | | |
|---|---|---|---|
| INCI name | Product name | wt.-% | Manufacturer/ supplier |
| Phase A | | | |
| Castor Oil | Castor oil | 43.70 | Honeywell Riedel-de Haen |
| Ethylhexyl Palmitate | Cegesoft C24 | 6.00 | Cognis |
| *Cocos Nucifera* (Coconut) Oil | Lipovol C-76 | 7.00 | Lipo Chemicals |
| Cera Alba | Ewacera 12 | 6.00 | H. Erhard Wagner |
| Isopropyl Lanolate | Ewalan IP | 5.00 | H. Erhard Wagner |
| *Persea Gratissima* (Avocado) Oil and Hydrogenated Vegetable Oil | Avocado Butter | 7.00 | Impag |
| Magnesium Stearate | Magnesium stearate | 3.00 | Sigma-Aldrich |
| Bis-Hydroxyethoxypropyl Dimethicone | Dow Corning 5562 Carbinol Fluid | 7.00 | Dow Corning |
| Dimethicone/Vinyl Dimethicone Crosspolymer and Silica | Dow Corning 9701 Cosmetic Powder | 5.00 | Dow Corning |
| Phenoxyethanol (and) Methylparaben (and) Ethylparaben (and) Butylparaben (and) Probylparaben (and) Isobutylparaben | Uniphen P-23 | 0.30 | Induchem |
| Phase B | | | |
| Copper-containing metal pigment according to Example 3 | | 10.00 | |

The pigment can be used in a range of from 5 to 22.0 wt.-%, relative to the total weight of the formulation. The balance can be made up with castor oil.

Phase A was mixed and heated to 85° C., Phase B was then added to Phase A accompanied by stirring. After being poured into a corresponding container, the mixture is cooled to room temperature.

Example 19: Application Example—Shower Gel

TABLE 11

| \multicolumn{4}{c}{Application example - Shower gel} | | | |
|---|---|---|---|
| INCI name | Product name | wt.-% | Manufacturer/ supplier |
| Phase A | | | |
| | Copper-containing metal pigment according to Example 3 | 0.50 | |
| Aqua | Water | 58.10 | |
| Acrylates Copolymer | Carbopol Aqua SF-1 | 5.50 | Lubrizol |
| Phase B | | | |
| Sodium Hydroxide | NaOH (10 wt.-%) | 1.50 | |
| Phase C | | | |
| Sodium Laureth Sulfate | Texapon NSO | 22.00 | Cognis |
| Cocamidopropyl Betaine | Tego Betain F 50 | 6.00 | Evonik |
| PEG-7 Glyceryl Cocoate | Emanon HE | 2.00 | Kao Corp. |
| Disodium Laureth Sulfosuccinate | Sectacin 103 Spezial | 2.00 | Zschimmmer & Schwarz |
| Phase D | | | |
| Phenoxyethanol (and) Piroctone Olamine | Nipaguard PO 5 | 0.60 | Clariant |
| Fragrance | Water Lily OA | 0.20 | Bell Flavors and Fragrances |
| Sodium Chloride | Sodium chloride | 1.60 | VWR |

The pigment can be used in a range of from 0.01 to 1.0 wt.-%, relative to the total weight of the formulation. The balance can be made up with water.

Phase A was mixed and stirred. Phase B was then added and stirred until a homogeneous appearance was achieved. Phase C was weighed out separately, mixed and added to Phase AB. The mixture can then be stirred again and Phase D was added individually.

Example 20: Application Example—Pressed Eyeshadow

TABLE 12

Application example - Pressed eyeshadow

| INCI name | Product name | wt.-% | Manufacturer/Supplier |
|---|---|---|---|
| Phase A | | | |
| Mica | Silk Mica | 17.00 | VWR |
| Boron Nitride | Softouch CCS 102 | 2.50 | Momentive |
| Zinc Stearate | Zinc stearate | 7.00 | VWR |
| Talc | Talcum powder | 43.50 | Sigma-Aldrich |
| | Copper-containing metal pigment according to Example 3 | 20.00 | |
| Phase B | | | |
| Dimethicone | Xiameter PMX-200 Silicone Fluid 5cs | 5.00 | Dow Corning |
| Cyclopentasiloxane (and) Dimethicone Crosspolymer | Dow Corning 9040 Elastomer | 5.00 | Dow Corning |

The pigment can be used in a range of from 5.0 to 40.0 wt.-%, relative to the total weight of the formulation. The balance can be made up with talc.

Phase A was mixed for 30 s at 2500 rpm in a high-speed mixer. Phase B was then added and the mixture mixed for 60 s at 3000 rpm in the same mixer. Lastly, the powder mixture is pressed into shape by means of an eyeshadow press at 150 bar for 30 s.

Example 21: Application Example—Hair Mascara

TABLE 13

Application example - Hair mascara

| INCI name | Product name | wt.-% | Manufacturer/supplier |
|---|---|---|---|
| Phase A | | | |
| Polyquaternium-16 | Luviquat FC 905 (Luviquat Exellence) | 2.70 | BASF |
| Propylene glycol | 1,2-propanediol | 1.80 | VWR |
| Methylparaben | Methyl-4-hydroxybenzoate | 0.20 | Sigma-Aldrich |
| Aqua | Water | 64.45 | |
| Phase B | | | |
| Cetearyl Alcohol | Lanette O | 5.00 | Cognis |
| Dimethicone | Xiameter PMX-200 Silicone Fluid 350cs | 1.00 | Dow Corning |
| Ceteareth-25 | Cremophor A 25 | 2.00 | BASF |
| Propylparaben | Propyl-4-hydroxybenzoate | 0.10 | Sigma-Aldrich |

TABLE 13-continued

Application example - Hair mascara

| INCI name | Product name | wt.-% | Manufacturer/supplier |
|---|---|---|---|
| Phase C | | | |
| Hydroxypropylcellulose | Klucel G | 0.50 | Ashland |
| Magnesium Aluminium Silicate | Veegum HV | 0.50 | R. T. Vanderbilt |
| Aqua | Water | 19.00 | |
| Phase D | | | |
| | Copper-containing metal pigment according to Example 3 | 2.50 | |
| Phenoxyethanol (and) Methylparaben (and) Butylparaben (and) Ethylparaben (and) Propylparaben (and) Isobutylparaben | Phenonip | 0.20 | Clariant |
| Fragrance | Blue Shadow OKO | 0.05 | Bell Flavors and Fragrances |

The pigment can be used in a range of from 1.0 to 10.0 wt.-%, relative to the total weight of the formulation. The balance can be made up with the water from Phase A.

Phase A and Phase B were heated separately to 80° C., then Phase B was slowly added to Phase A. In a separate vessel, Klucel and Veegum were added to the water from Phase C. Phase AB was then cooled to 40° C. and, during the cooling, Phases C and D were added accompanied by stirring.

Example 22: Application Example—Hair Gel

TABLE 14

Application example - Hair gel

| INCI name | Product name | wt.-% | Manufacturer/supplier |
|---|---|---|---|
| Phase A | | | |
| | Copper-containing metal pigment according to Example 2 | 0.10 | |
| Ammonium Acryloyldimethyltaurate/VP Copolymer | Aristoflex AVC | 1.40 | Clariant |
| Citric Acid | Citric acid | 0.10 | VWR |
| Aqua | Water | 55.10 | |
| Phase B | | | |
| PVP | Luviskol K 30 Powder | 1.50 | BASF |
| Propylene Glycol, Diazolidinyl, Urea, Methylparaben, Propylparaben | Germaben II | 0.20 | International Speciality Products |
| Triethanolamine | Triethanolamine | 1.20 | VWR |
| Water | Water | 40.40 | |

The pigment can be used in a range of from 0.01 to 2.0 wt.-%, relative to the total weight of the formulation. The balance can be made up with water.

The pigment was stirred with water from Phase A, Aristoflex AVC and citric acid were added accompanied by stirring and mixed at a speed of 800 rpm for 15 minutes. Phase B was dissolved until a homogeneous solution formed, then Phase B was added to Phase A and mixed.

Example 23: Application Example—Body Powder

TABLE 15

Application example - Body powder

| INCI name | Product name | wt.-% | Manufacturer/ supplier |
|---|---|---|---|
| Phase A | | | |
| Mica | Silk Mica | 58.70 | VWR |
| Talc | Talcum powder | 18.00 | Sigma-Aldrich |
| Boron Nitride | Softouch CCS 102 | 5.00 | Advanced Ceramics |
| Nylon-12 | Orgasol 2002 D/Nat | 8.00 | Arkema |
| Magnesium Stearate | Magnesium stearate | 6.00 | Sigma-Aldrich |
| Methylparaben, Propylparaben | Rokonsal SSH-1 | 0.30 | ISP Biochema |
| | Copper-containing metal pigment according to Example 2 | 2.00 | |
| Phase B | | | |
| Tridecyl Stearate (and) Tridecyl Trimellitate (and) Dipentaerythrityl Hexacaprylate/ Hexacaprate | Lipovol MOS-130 | 2.00 | Lipo Chemicals |

The pigment can be used in a range of from 0.2 to 5.0 wt.-%, relative to the total weight of the formulation. The balance can be made up with silk mica.

Phase A was mixed, then Phase B was added to Phase A and the mixture was then poured into a suitable vessel.

Example 24: Application Example—Lip Gloss

TABLE 16

Application example - Lip gloss

| INCI name | Product name | wt.-% | Manufacturer/ supplier |
|---|---|---|---|
| Phase A | | | |
| Hydrogenated Polyisobutene (and) Ethylene/Propylene/ Styrene Copolymer (and) Butylene/Ethylene/ Styrene Copolymer | Versagel ME 750 | 79.00 | Calumet Penreco |
| Simmondsia Chinensis (Jojoba) Seed Oil | Jojoba Oil - Natural/Golden | 2.00 | BioChemica |
| Caprylyl Trimethicone | Silcare Silicone 31M50 | 7.00 | Clariant |
| Stearyl Dimethicone | Silcare Silicone 41M65 | 3.20 | Clariant |
| Hydrogenated Polydecene | Nexbase 2002 | 4.00 | Jan Dekker |
| Isopropyl Myristate | Isopropyl myristate | 4.50 | VWR |
| Phase B | | | |
| | Copper-containing metal pigment according to Example 2 | 0.10 | |
| Propylparaben | Propyl-4-hydroxybenzoate | 0.20 | Sigma-Aldrich |

The pigment can be used in a range of from 0.10 to 8.00 wt.-%, relative to the total weight of the formulation. The balance can be made up with Versagel ME 750.

Phase A was heated to 85° C., then the contents of Phase B were added individually to Phase A, followed by stirring until a uniform consistency formed and then pouring into a lip gloss container.

Example 25: Application Example—Lip Liner

TABLE 17

Application example - Lip liner

| INCI name | Product name | wt.-% | Manufacturer/ supplier |
|---|---|---|---|
| Phase A | | | |
| Hydrogenated Coco-Glycerides | Softisan 100 | 12.35 | Sasol Wax |
| Candelilla Cera | Ewacera 42 | 14.00 | H. Erhard Wagner |
| Magnesium Stearate | Magnesium stearate | 6.00 | Sigma-Aldrich |
| Stearic Acid | Kortacid 1895 | 8.50 | Akzo Nobel |
| Hydrogenated Coconut Oil | Lipex 401 | 8.00 | Aarhus Karlshamn |
| Cetyl Palmitate | Kahlwax 7157 | 7.00 | Kahl |
| Caprylic/Capric Triglyceride | Liponate GC-K | 3.60 | Lipo Chemicals |
| Soybean Glycerides (and) Butyrospermum Parkii | Lipex L'sens | 15.00 | Aarhus Karlshamn |
| Tocopheryl Acetate | dl-alpha-Tocopheryl acetate | 0.25 | Jan Dekker |
| Methylparaben; Propylparaben | Rokonsal SSH-1 | 0.30 | ISP Biochema |
| Phase B | | | |
| | Copper-containing metal pigment according to Example 3 | 25.00 | |

The pigment can be used in a range of from 15 to 25 wt.-%, relative to the total weight of the formulation. Alternatively, further color and/or effect pigments in addition to the pigment can be added. The maximum pigmentation level should, however, not be exceeded.

Phase A was heated to 85° C. and then Phase B was added to Phase A accompanied by stirring until a uniform material resulted. The mixture was then poured, hot, into a pencil mold.

Example 26: Application Example—Lipstick

TABLE 18

Application example - Lipstick

| INCI name | Product name | wt.-% | Manufacturer/ supplier |
|---|---|---|---|
| Phase A | | | |
| Carnauba Wax | Ewacera 34 | 4.50 | H. Erhard Wagner |
| Cera Alba | Ewacera 12 | 3.50 | H. Erhard Wagner |
| Candelilla Cera Extract | Ewacera 42 | 4.00 | H. Erhard Wagner |
| Microcrystalline Wax | TeCero-Wax 1030 K | 7.20 | TH.C. Tromm |
| Cetyl Palmitate | Kahlwax 7157 | 2.00 | Kahl |

TABLE 18-continued

Application example - Lipstick

| INCI name | Product name | wt.-% | Manufacturer/supplier |
|---|---|---|---|
| Hydrogenated Coco-Glycerides | Softisan 100 | 5.00 | Sasol Wax |
| Petrolatum | Penreco Blond | 5.80 | Calumet Penreco |
| Cetearyl Ethylhexanoate | Luvitol EHO | 10.70 | BASF |
| Tocopheryl Acetate | dl-alpha-tocopheryl acetate | 0.50 | Jan Dekker |
| Castor Oil | Castor oil | 46.60 | Honeywel Riedel-de Haen |
| Phase B | | | |
| | Copper-containing metal pigment according to Example 2 | 10.00 | |
| Methylparaben, Propylparaben | Rokonsal SSH-1 | 0.20 | ISP Biochema |

The pigment can be used in a range of from 0.5 to 21.0 wt.-%, relative to the total weight of the formulation. The balance can be made up with castor oil.

Phase A was heated to 85° C., then Phase B was added to Phase A and mixed. This mixture was then poured, at a temperature of 75° C., into a lipstick mold.

Example 27: Application Example—Liquid Eyeliner

TABLE 19

Application example - Liquid eyeliner

| INCI name | Product name | wt.-% | Manufacturer/supplier |
|---|---|---|---|
| Phase A | | | |
| Aqua | Water | 66.70 | |
| Water/carbon black dispersion | MBD 201 | 3.00 | Geotech |
| Acrylates Copolymer | Covacryl E14 | 10.00 | LCW |
| Magnesium Aluminium Silicate | Veegum HV | 1.00 | C. H. Erbsloh |
| Phase B | | | |
| Propylene Glycol | 1,2-propanediol | 3.00 | VWR |
| Triethanolamine | Triethanolamine | 1.40 | VWR |
| Phase C | | | |
| Xanthan Gum | Keltrol CG-T | 0.30 | CP Kelco |
| Phase D | | | |
| | Copper-containing metal pigment according to Example 3 | 3.00 | |
| Mica | Silk Mica | 2.00 | VWR |
| Phase E | | | |
| Stearic Acid | Kortacid 1895 | 2.80 | Akzo Nobel |
| Glyceryl Stearate | Aldo MS K FG | 0.80 | Lonza |
| Oleyl Alcohol | HD-Ocenol 90/95 V | 0.50 | Cognis |
| Phenoxyethanol (and) Methylparaben (and) Ethylparaben (and) Butylparaben (and) Probylparaben (and) Isobutylparaben | Uniphen P-23 | 0.50 | Induchem |
| Phase F | | | |
| Dimethicone (and) Trisiloxane | Xiameter PMX-1184 Silicone Fluid | 5.00 | Dow Corning |

The pigment can be used in a range of from 0.5 to 8.0 wt.-%, relative to the total weight of the formulation. The balance can be made up with water.

Veegum was dispersed in Phase A and stirred for 15 minutes, then Phase B was added to Phase A, then Phase C to Phase AB and stirred again for 10 minutes. Phase D was then added to Phase ABC and heated to 75° C. Next, phase E was also heated to 75° C. and added to Phase ABCD. After cooling to 60° C., Phase F was added and the mixture poured into a suitable vessel.

Example 28: Application Example—Mousse

TABLE 20

Application example - Mousse

| INCI name | Product name | wt.-% | Manufacturer/supplier |
|---|---|---|---|
| Phase A | | | |
| Cyclopentasiloxane | Xiameter PMX-0245 Cyclosiloxane | 8.60 | Dow Corning |
| Hydrogenated Polyisobutene | MC 30 | 4.00 | www.sophim.com |
| Dimethicone (and) Dimethicone Crosspolymer | Dow Corning 9041 Silicone Elastomer Blend | 37.14 | Dow Corning |
| Squalane | Squalane | 5.74 | Impag |
| Isononyl Isononanoate | Dermol 99 | 10.16 | Alzo International |
| Hydrogenated Jojoba Oil | Jojoba Butter LM | 2.15 | Desert Whale |
| Hydrogenated Jojaba Oil | Jojoba Butter HM | 1.00 | Desert Whale |
| C30-45 Alkyl Methicone (and) C30-45 Olefin | Dow Corning AMS-C30 Cosmetic Wax | 1.15 | Dow Corning |
| Stearyl Dimethicone | Dow Corning 2503 Cosmetic Wax | 0.47 | Dow Corning |
| Cyclopentasiloxane (and) Polypropylsilsesquioxane | Dow Corning 670 Fluid | 5.00 | Dow Corning |

TABLE 20-continued

Application example - Mousse

| INCI name | Product name | wt.-% | Manufacturer/supplier |
|---|---|---|---|
| Phase B | | | |
| Dimethicone/Vinyl Dimethicone Crosspolymer | Dow Corning 9506 Powder | 16.02 | Dow Corning |
| Silica Dimethyl Silylate | Covasilic 15 | 0.17 | LCW |
| Talc | Talcum powder | 5.00 | Sigma-Aldrich |
| | Copper-containing metal pigment according to Example 2 | 3.00 | |
| Phase D | | | |
| Propylene Glycol, Diazolidinyl Urea, Methylparaben, Propylparaben | Germaben II | 0.40 | International Speciality Products |

The pigment can be used in a range of from 0.1 to 8.0 wt.-%, relative to the total weight of the formulation. The balance can be made up with Dow Corning 9041 elastomer.

Phase A was mixed and heated until everything had melted. Phase B was weighed out separately and mixed with a high-speed mixer for 60 s at 2400 rpm. Half of the melted Phase A was added to Phase B and mixed again in the mixer at 2400 rpm for 30 s. Then, the remaining part of Phase B was also added to Phase A and mixed again at 2400 rpm for 30 s. Lastly, Phase C is added to Phase AB and mixed again at 2400 rpm for 30 s in the high-speed mixer.

Example 29: Application Example—Nail Polish

TABLE 21

Application example - Nail polish

| INCI name | Product name | wt.-% | Manufacturer/supplier |
|---|---|---|---|
| Phase A | | | |
| | Copper-containing metal pigment according to Example 2 | 2.00 | |
| Phase B | | | |
| Butyl Acetate (and) Ethyl Acetate (and) Nitrocellulose (and) Isopropyl Alcohol | International Lacquers Nailpolish & Care Base 359 | 98.00 | International Lacquers |

The pigment can be used in a range of from 0.1 to 10.0 wt.-%, relative to the total weight of the formulation. The balance can be made up with International Lacquers nail polish.

Phase A and Phase B were mixed and then poured into an appropriate container.

Example 30: Application Example—Nail Polish with "Soft Touch" Effect

TABLE 22

Application example - Nail polish with "soft touch" effect

| INCI name | Product name | wt.-% | Manufacturer/supplier |
|---|---|---|---|
| Phase A | | | |
| | Copper-containing metal pigment according to Example 2 | 2.00 | |
| | Ceraflour 913 | 5.00 | Byk Chemie |
| Phase B | | | |
| Butyl Acetate (and) Ethyl Acetate (and) Nitrocellulose (and) Isopropyl Alcohol | International Lacquers Nailpolish & Care Base 359 | 93.00 | International Lacquers |

The pigment can be used in a range of from 0.1 to 10.0 wt.-%, relative to the total weight of the formulation. The balance can be made up with International Lacquers nail polish.

Example 31: Application Example—Aqueous Nail Polish

The pigment can be used in an aqueous nail polish according to WO 2007/115675 A2, Example 1. The pigmentation level here is 0.1 to 10.0 wt.-%, for example 1.5 wt.-%, relative to the total weight of the formulation.

Example 32: Application Example—Liquid Eyeshadow

TABLE 23

Application example - Liquid eyeshadow

| INCI name | Product name | wt.-% | Manufacturer/supplier |
|---|---|---|---|
| Phase A | | | |
| Water | Water | 70.10 | |
| Glycerin | Pricerine 9090 | 6.00 | Croda |

TABLE 23-continued

Application example - Liquid eyeshadow

| INCI name | Product name | wt.-% | Manufacturer/supplier |
|---|---|---|---|
| Phase B | | | |
| PEG-800 | Polyglycol 35000 S | 0.60 | Clariant |
| Allantoin | Allantoin | 0.30 | 3V |
| Ammonium Acryloyldimethyltaurate/VP Copolymer | Aristoflex AVC | 0.80 | Clariant |
| Acrylates Copolymer | Worlee Micromer CEK 20/50 | 5.00 | Worlee |
| Phase C | | | |
| | Copper-containing metal pigment according to Example 2 | 10.00 | |
| Divinyldimethicone/Dimethicone Copolymer C12-C13 Pareth-3, C12-C13 Pareth-23 | Dow Corning HMW 2220 Non-Ionic Emulsion | 6.00 | Dow Corning |
| Fragrance | Water Lily OA | 0.20 | Bell Flavors and Fragrances |
| Phenoxyethanol (and) Methylparaben (and) Butylparaben (and) Ethylparaben (and) Propylparaben (and) Isobutylparaben | Phenonip | 1.00 | Clariant |

The pigment can be used in a range of from 0.10 to 17.00 wt.-%. The balance can be made up with water.

Phase A was stirred, then the contents of Phase B were added individually to Phase A and stirred until a uniform consistency formed. The contents of Phase C were then added individually to Phase AB and stirred until a uniform consistency formed again.

The invention claimed is:

1. A coated platelet-shaped copper-containing metal pigment, wherein the copper-containing metal pigment is selected from the group consisting of copper pigments, brass pigments, oxidized copper pigments, oxidized brass pigments and mixtures thereof and has an elemental copper content of at least 50 weight percent, relative to the weight of uncoated copper-containing metal pigment, wherein the coated copper-containing metal pigment comprises a coating comprising at least one enveloping silicon oxide layer, wherein the silicon oxide layer is selected from the group consisting of silicon oxide, hydroxides thereof, and mixtures thereof, and at least one enveloping chemically non-reactive plastic layer, wherein the at least one plastic layer comprises polyacrylate, polymethacrylate, or a mixture thereof, wherein the at least one enveloping chemically non-reactive plastic layer is formed on the platelet-shaped copper-containing pigments coated with at least one enveloping silicon oxide layer, by polymerizing (meth)acrylate monomers or reactive (meth)acrylate oligomers, and optionally polymerization initiators, in the presence of the platelet-shaped copper-containing pigments coated with at least one enveloping silicon oxide layer, wherein the sum of the amounts of the at least one chemically non-reactive plastic layer and of the at least one silicon oxide layer lies in a range of from 10 to 50 weight percent, relative to the weight of the uncoated metal pigment, and the weight ratio of the at least one silicon oxide layer to the at least one chemically non-reactive plastic layer lies in a range of from 1:2 to 1:20.

2. The coated platelet-shaped copper-containing metal pigment according to claim 1, wherein the at least one enveloping silicon oxide layer is arranged between the copper-containing metal pigment and the at least one chemically non-reactive plastic layer.

3. The coated platelet-shaped copper-containing metal pigment according to claim 1, wherein the at least one chemically non-reactive plastic layer is arranged between the copper-containing metal pigment and the at least one enveloping silicon oxide layer.

4. The coated platelet-shaped copper-containing metal pigment according to claim 1, wherein the weight proportion of the at least one enveloping silicon oxide layer lies in a range of from 0.9 to 12 weight percent, relative to the weight of the uncoated copper-containing metal pigment.

5. The coated platelet-shaped copper-containing metal pigment according to claim 1, wherein the weight proportion of the at least one enveloping silicon oxide layer in platelet-shaped copper-containing metal pigment in which a chemically non-reactive plastic layer forms a top layer of the coating lies in a range of from 0.9 to 12 weight percent and in platelet-shaped copper-containing metal pigment in which a silicon oxide layer forms a top layer of the coating lies in a range of from 1.0 to 10 weight percent.

6. The coated platelet-shaped copper-containing metal pigment according to claim 1, wherein the weight ratio of the at least one enveloping plastic layer lies in a range of from 8 to 40 weight percent, relative to the weight of the uncoated copper-containing metal pigment.

7. The coated platelet-shaped copper-containing metal pigment according to claim 1, and wherein the weight ratio of the at least one silicon oxide layer to the at least one chemically non-reactive plastic layer lies in a range of from 1:2.2 to 1:17.

8. The coated platelet-shaped copper-containing metal pigment according to claim 7, wherein the sum of the amount of the at least one chemically non-reactive plastic layer and the amount of the at least one silicon oxide layer lies in a range of from 13 to 40 weight percent, relative to the weight of the uncoated metal pigment.

9. The coated platelet-shaped copper-containing metal pigment according to claim 7, wherein the weight ratio of the at least one silicon oxide layer to the at least one chemically non-reactive plastic layer lies in a range of from 1:2.5 to 1:15.

10. The coated platelet-shaped copper-containing metal pigment according to claim 7, wherein the weight proportion of the at least one silicon oxide layer lies in a range of from 1.5 to 9 weight percent, relative to the weight of the uncoated copper-containing metal pigment.

11. The coated platelet-shaped copper-containing metal pigment according to claim 7, wherein the weight proportion of the chemically non-reactive plastic layer lies in a range of from 10 to 35 weight percent, relative to the weight of the uncoated copper-containing metal pigment.

12. The coated platelet-shaped copper-containing metal pigment according to claim 7, wherein the at least one chemically non-reactive plastic layer is obtained by thermal polymerization.

13. The coated platelet-shaped copper-containing metal pigment according to claim 7, wherein the at least one chemically non-reactive plastic layer is obtained by initiator-induced radical polymerization.

14. A pigmented coating agent comprising at least one coated platelet-shaped copper-containing metal pigment according to claim 1.

15. A coated object comprising at least one coated platelet-shaped copper-containing metal pigment according to claim 1.

16. A process for producing a pigmented coating agent, comprising introducing the coated platelet-shaped copper-containing metal pigment according to claim 1 into a coating agent.

17. A process for producing a pigmented coating agent, according to claim 16, wherein the pigmented coating agent is a powder coating.

18. A process for producing a pigmented coating agent, according to claim 16, wherein the pigmented coating agent is a varnish for use in a coil-coating method.

19. A cosmetic product selected from the group consisting of body powder, face powder, pressed powder, loose powder, face makeup, powder cream, cream makeup, emulsion makeup, wax makeup, foundation, mousse makeup, blusher, eye makeup, eyeshadow, mascara, eyeliner, liquid eyeliner, eyebrow pencil, lip balm, lipstick, lip gloss, lip liner, hair styling compositions, hair spray, hair mousse, hair gel, hair wax, hair mascara, permanent hair dyes, semi-permanent hair dyes, temporary hair dyes, skin care compositions, lotions, gels, emulsions and nail polish compositions, the cosmetic product comprising at least one coated platelet-shaped copper-containing metal pigment according to claim 1.

20. The cosmetic product according to claim 19, wherein the cosmetic product is a nail polish composition.

21. A method for producing a coated platelet-shaped copper-containing metal pigment according to claim 1, comprising:
    (1a) coating platelet-shaped copper-containing metal pigment with silicon oxide, hydroxides thereof, or mixtures thereof,
    (1b) coating the platelet-shaped copper-containing metal pigment coated with silicon oxide, hydroxides thereof, or mixtures thereof obtained in step (1a) with the educt(s) of a chemically non-reactive plastic layer,
    (1c) curing or polymerizing the copper-containing metal pigment pigments coated with the educt(s) of the chemically non-reactive plastic layer in step (1 b),
    or
    (2a) coating platelet-shaped copper-containing metal pigment pigments with the educt(s) of the a chemically non-reactive plastic layer,
    (2b) curing or polymerizing the platelet-shaped copper-containing metal pigment pigments coated with the educt(s) of the chemically non-reactive plastic layer in step (2a),
    (2c) coating the platelet-shaped copper-containing metal pigment pigments coated with chemically non-reactive plastic layer obtained in step (2b) with silicon oxide, hydroxides thereof, or mixtures thereof.

22. The method for producing a coated platelet-shaped copper-containing metal pigment according to claim 21, wherein the educt or the educts of the chemically non-reactive plastic layer are monomers selected from the group consisting of vinyl-functional monomers, (meth)acrylate-functional monomers, and mixtures thereof and in that the curing or polymerization of the monomers takes place thermally during the production of the chemically non-reactive plastic layer.

23. The method for producing a coated platelet-shaped copper-containing metal pigment according to claim 21, wherein the curing or polymerization in step 1(c) or step 2(b) takes place by radical polymerization using polymerization initiators.

24. The coated platelet-shaped copper-containing metal pigment according to claim 1, wherein the plastic layer is prepared from at least one monomer selected from the group consisting of isoamyl acrylate, lauryl acrylate, stearyl acrylate, butoxyethyl acrylate, ethoxy diethylene glycol acrylate, methoxy triethylene glycol acrylate, methoxy polyethylene glycol acrylate, methoxy dipropylene glycol acrylate, phenoxyethyl acrylate, phenoxy polyethylene glycol acrylate, tetrahydrofurfuryl acrylate, isobornyl acrylate, 2-hydroxyethyl acrylate, 2-hydroxypropyl acrylate, 2-hydroxy-3-phenoxypropyl acrylate, 2-acryloyloxyethyl succinic acid, 2-acryloyloxyethyl phthalic acid, 2-acryloyloxyethyl-2-hydroxyethyl phthalic acid, triethylene glycol diacrylate, neopentyl glycol diacrylate, 1,6-hexanediol diacrylate, 1,9-nonanediol diacrylate, dimethylol tricyclodecane diacrylate, trimethylolpropane triacrylate, pentaerythritol triacrylate, pentaerythritol tetraacrylate, dipentaerythritol hexaacrylate, 2-hydroxy-3-acryloyloxy propyl methacrylate, isooctyl acrylate, isomyristyl acrylate, isostearyl acrylate, 2-ethyl hexyl diglycol acrylate, 2-hydroxybutyl acrylate, 2-acryloyloxyethyl hexahydrophthalic acid, hydroxy pivalic acid neopentyl glycol diacrylate, polytetraethylene glycol diacrylate, ditrimethylolpropane tetraacrylate, methyl methacrylate, ethyl methacrylate, n-butyl methacrylate, isobutyl methacrylate, 2-ethylhexyl methacrylate, isodecyl methacrylate, n-lauryl methacrylate, tridecyl methacrylate, n-stearyl methacrylate, methoxydiethylene glycol methacrylate, methoxy polyethylene glycol methacrylate, cyclohexyl methacrylate, tetrahydrofurfural methacrylate, benzyl methacrylate, phenoxyethyl methacrylate, isobornyl methacrylate, 2-hydroxyethyl methacrylate, 2-hydroxypropyl methacrylate, 2-hydroxybutyl methacrylate, 2-methacryloyloxyethyl succinic acid, 2-methacryloyloxyethyl hexahydrophthalic acid, 2-methacryloyloxyethyl-2-hydroxypropyl phthalate, ethylene glycol dimethacrylate, diethylene glycol dimethacrylate, 1,4-butanediol dimethacrylate, 1,3-butanediol dimethacrylate, 1,6-hexanediol dimethacrylate, 1,9-nonanediol dimethacrylate, trimethylolpropane trimethacrylate, glycerol dimethacrylate, 2-hydroxy-3-acryloyloxy propyl methacrylate, t-butyl methacrylate, isostearyl methacrylate, methoxytriethylene glycol methacrylate, n-butoxyethyl methacrylate, 3-chloro-2-hydroxypropyl methacrylate, triethylene glycol dimethacrylate, neopentyl glycol dimethacrylate, acrylic acid, methacrylic acid, and mixtures thereof.

25. The coated platelet-shaped copper-containing metal pigment according to claim 1, wherein the plastic layer is prepared from at least one monomer selected from the group consisting of 1,6-hexanediol diacrylate, 1,9-nonanediol diacrylate, dimethylol tricyclodecane diacrylate, neopentyl glycol dimethacrylate, trimethylolpropane triacrylate, trimethylolpropane trimethacrylate and mixtures thereof.

26. The coated platelet-shaped copper-containing metal pigment according to claim 24, wherein the at least one plastic layer is prepared from at least one monomer and at least one adhesion promoter selected from the group consisting of organofunctional silanes, aluminates, phosphonic acids, phosphoric acid esters, zirconates and mixtures thereof.

27. The coated platelet-shaped copper-containing metal pigment according to claim 1, further comprising at least one layer prepared from at least one adhesion promoter selected from the group consisting of organofunctional silanes, aluminates, phosphonic acids, phosphoric acid esters, zirconates and mixtures thereof, the layer being positioned between the at least one enveloping silicon oxide layer and the at least one enveloping chemically non-reactive plastic layer.

* * * * *

UNITED STATES PATENT AND TRADEMARK OFFICE
CERTIFICATE OF CORRECTION

PATENT NO. : 9,777,160 B2  
APPLICATION NO. : 14/007300  
DATED : October 3, 2017  
INVENTOR(S) : Oliver Struck et al.

Page 1 of 1

It is certified that error appears in the above-identified patent and that said Letters Patent is hereby corrected as shown below:

In the Claims

Column 55, Line 42, Claim 21, after "the" delete "a"

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*